(12) United States Patent
McCann

(10) Patent No.: US 9,683,933 B2
(45) Date of Patent: Jun. 20, 2017

(54) METHOD AND APPARATUS FOR DETECTING AN ANALYTE

(71) Applicant: The Board of Regents of the University of Oklahoma, Norman, OK (US)

(72) Inventor: Patrick J. McCann, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 368 days.

(21) Appl. No.: 14/067,827

(22) Filed: Oct. 30, 2013

(65) Prior Publication Data
US 2014/0117238 A1   May 1, 2014

Related U.S. Application Data

(60) Provisional application No. 61/720,298, filed on Oct. 30, 2012.

(51) Int. Cl.
*G01N 21/35*   (2014.01)
*G01N 21/3504*   (2014.01)

(52) U.S. Cl.
CPC ............... *G01N 21/3504* (2013.01)

(58) Field of Classification Search
CPC ........................................... G01N 1/3504
See application file for complete search history.

(56) References Cited

U.S. PATENT DOCUMENTS

| | | | | |
|---|---|---|---|---|
| 3,638,026 A * | 1/1972 | Scott et al. | ............. | H01L 21/00 136/249 |
| 6,150,659 A * | 11/2000 | Baliga | ................... | G01J 1/1626 250/339.15 |
| 8,420,926 B1 * | 4/2013 | Reedy | ................... | H01L 31/052 136/248 |
| 2003/0134427 A1 * | 7/2003 | Roller | ................ | G01N 21/3504 436/171 |
| 2012/0055528 A1 * | 3/2012 | McCann | ................. | H01L 35/16 136/238 |
| 2013/0247951 A1 * | 9/2013 | McCann | ................. | H01L 35/26 136/238 |
| 2014/0049777 A1 * | 2/2014 | Sun | ........................... | G01J 3/42 356/409 |

\* cited by examiner

*Primary Examiner* — Yara B Green
(74) *Attorney, Agent, or Firm* — Dunlap Codding, P.C.

(57) ABSTRACT

Disclosed herein are methods and mid-IR detection apparatus to measure analytes in gas or liquid phase. Solid state cooling of a crystalline lattice is effectively achieved with the controlled flow of charge carriers that absorb thermal energy from the semiconductor material which senses mid-IR photons. Reduction in temperature improves signal-to-noise ratios thus improving molecular sensitivity. In one embodiment the apparatus is used to detect a biomarker.

33 Claims, 21 Drawing Sheets

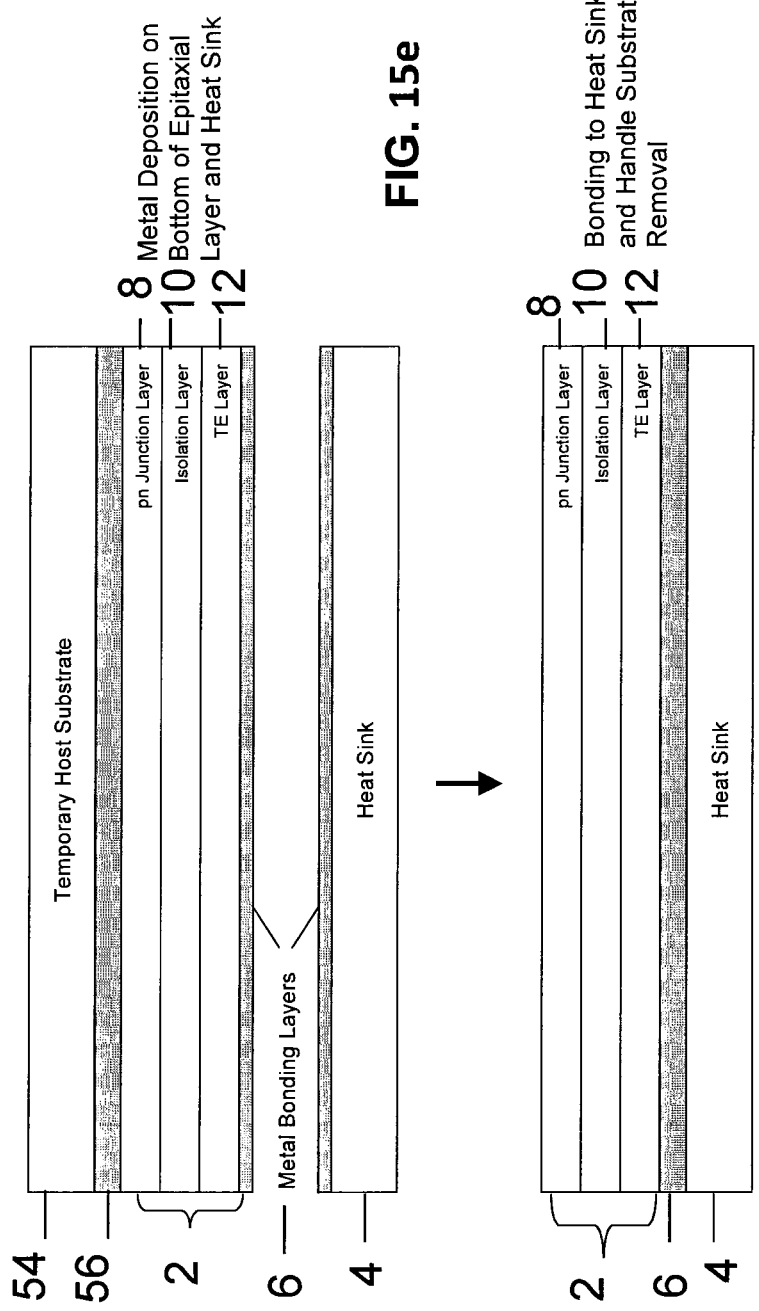

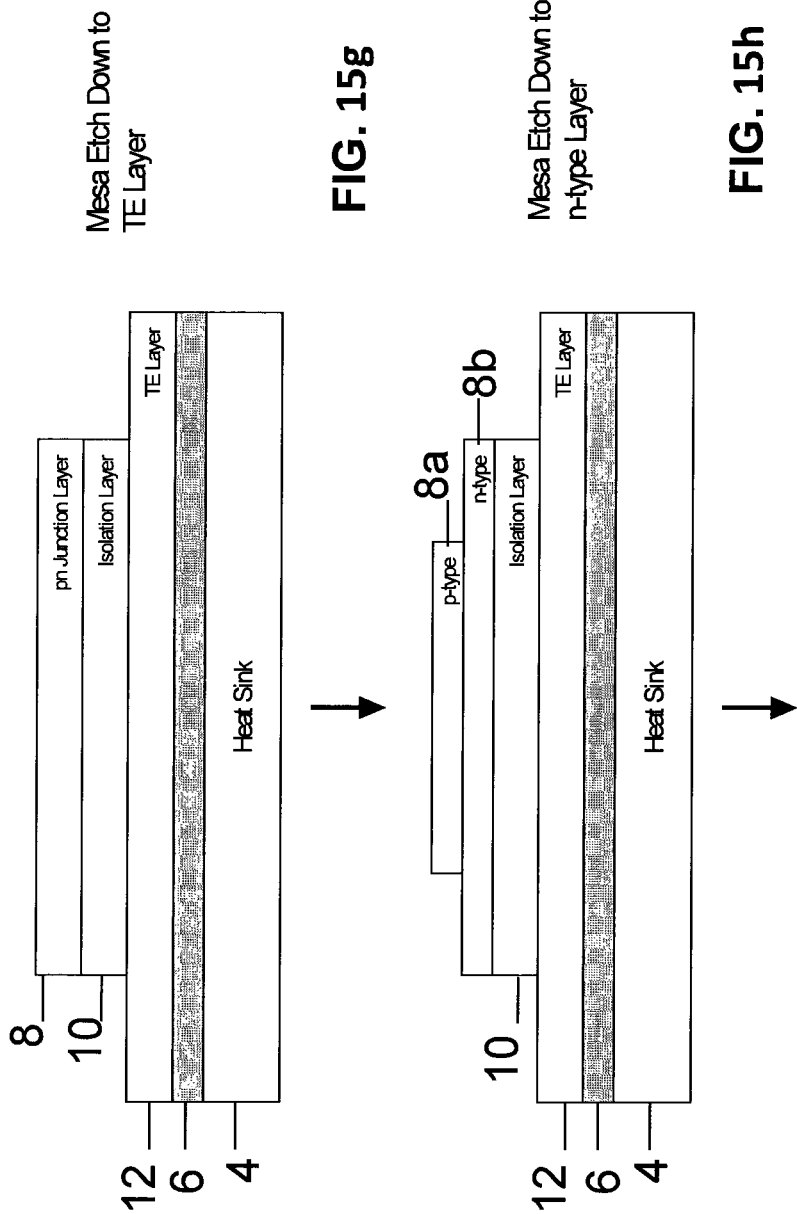

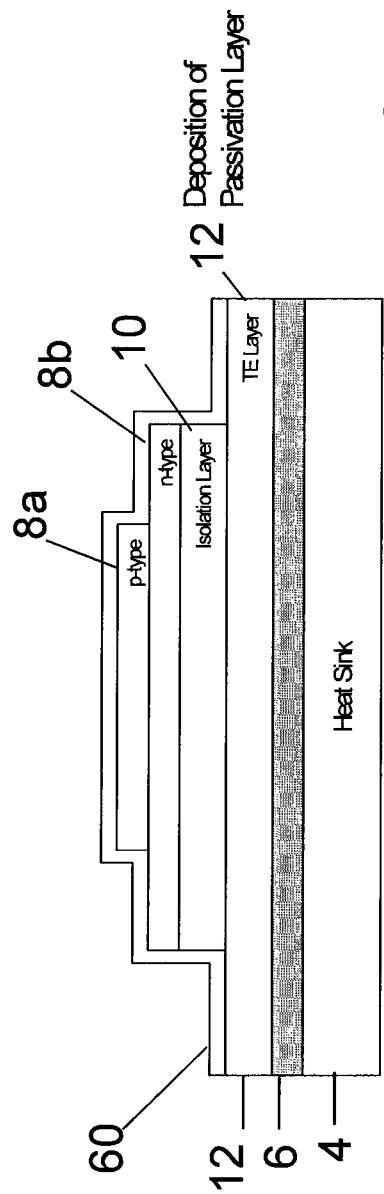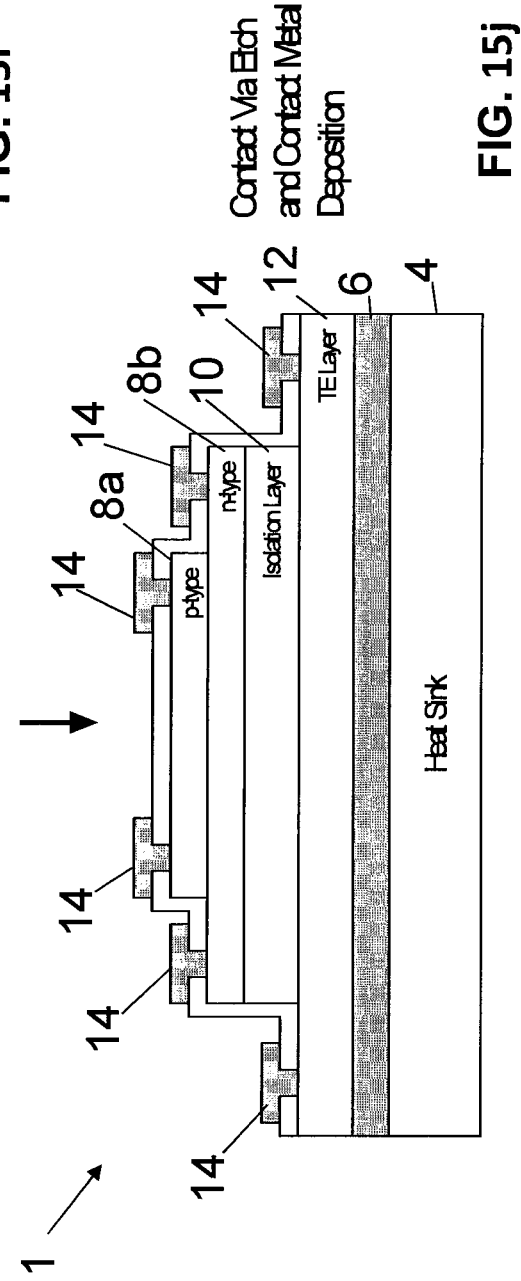

METHOD AND APPARATUS FOR DETECTING AN ANALYTE

INCORPORATION OF RELATED APPLICATIONS

The present patent application incorporates by reference the entire provisional patent application identified by U.S. Ser. No. 61/720,298 filed on Oct. 30, 2012.

FIELD OF DISCLOSURE

The present disclosure relates to methods and apparatus for using a mid-IR sensor to detect and/or measure analytes in samples, including but not limited to analytes which correspond to metabolic changes.

BACKGROUND

Otto Warburg published a paper in 1927 that described the accumulation of lactate in the veins of experimental rats that had growing cancer cells. He explained this observation by concluding that cancer cells obtained metabolic energy from an aerobic glycolysis (i.e. fermentation) mechanism. This was a new phenomenon that was unique to cancer because glycolysis was normally observed to occur under anaerobic conditions, which is known as the Pasteur Effect (where oxygen inhibits glycolysis). Interest in further investigation of the Warburg effect has increased significantly over the last ten years. Recent studies have uncovered some of the biochemical mechanisms associated with aerobic glycolysis and cancer.

Warburg devoted his life to measuring and understanding energy flow through biological systems. Some of his measurement techniques came from the same laboratory where precision blackbody radiation measurements were performed at the end of the 19$^{th}$ century. Max Planck used data from this lab in 1900 to derive his law of radiation and calculate the value of 'quantum action', $h=6.63\times10^{-34}$ J s, work that launched the development of quantum mechanics (the field of physics that is used to design and fabricate the laser devices discussed below). In addition to optical measurement techniques, Warburg developed and used manometers to measure oxygen consumption, and thus energy input, of a variety of biological systems. His experiments had the unifying theme of understanding chemical energy flow through a biological system. Much of our textbook understanding of biological metabolism can trace its origins to work in his laboratory.

Injured Respiration

In a paper titled "On the Origin of Cancer Cells" published in Science in 1956, Warburg offers this summary:

The irreversible injuring of respiration is followed, as the second phase of cancer formation, by a long struggle for existence by the injured cells to maintain their structure, in which part of the cells perish from lack of energy, while another part succeed in replacing the irretrievably lost respiration energy by fermentation energy. Because of the morphological inferiority of fermentation energy, the highly differentiated body cells are converted by this into undifferentiated cells that grow wildly—the cancer cells.

FIG. 1 illustrates the respiration process for a healthy cell. It begins with the breakdown of glucose to pyruvate through the glycolysis mechanism where a small amount of energy for cell function, as represented by two adenosine triphosphate (A TP) molecules generated for each glucose molecule, is produced. Pyruvate then enters the respiration mechanism by interacting with pyruvate dehydrogenase (POH) resulting in conversion of pyruvate to acetyl-CoA, which is the molecule that enters the tricarboxylic acid (TCA) (or Krebs) cycle. This cycle is very efficient, producing up to 36 ATP molecules for each glucose molecule.

FIG. 2 illustrates a cell with injured respiration. In this case pyruvate does not enter the Krebs cycle. Instead it is shown to form lactate, which is the molecule that Warburg measured to identify the fermentation phenotype for cancer cells. He also observed that the rate of glycolysis for this phenotype was much higher than when respiration is not impaired. As a result, growing cancer cells can still receive sufficient energy even though the ATP-producing mechanism is not as efficient. This higher rate of glycolysis provides the scientific basis for positron emission tomography (PET) scans that reveal images of cancerous tumors. The technique involves administering a radiolabeled glucose analog [$^{18}$F]-fluorodeoxyglucose (FOG) where the high rate of glycolysis within tumors concentrates the positron-emitting fluorine isotope. The widespread clinical success of PET scans offers convincing experimental confirmation of the selective high uptake of glucose in invasive tumors.

Underlying Cause of Injured Respiration

Hans Krebs, who worked in Otto Warburg's laboratory as a postdoctoral associate from 1926 to 1930, uncovered a variety of cyclic mechanisms in biological systems including the Krebs cycle (also known by other names such as the TCA or citric acid cycle or oxidative phosphorylation) while at universities in Freiburg, Germany and Oxford, England. In his 1981 biography of Otto Warburg, Krebs offered this opinion on Warburg's cancer theory:

Warburg's 'primary cause of cancer'—the replacement of respiration by fermentation—may be a symptom of the primary cause, but is not the primary cause itself. The primary cause is to be expected at the level of the control of gene expression, the minutiae of which are unknown though some of the principles involved are understood.

As mentioned above, pyruvate enters the respiration mechanism by interacting with PDH resulting in conversion of pyruvate to acetyl-CoA. Recent research has provided some minutiae, as suggested by Krebs 25 years earlier, of the underlying genetic cause of injured respiration. By performing a series of measurements with mouse embryo fibroblasts, it has been shown that hypoxia-inducible factor 1 (HIF-1), a genetic transcription factor that responds to decreases in oxygen supply, induces pyruvate dehydrogenase kinase 1 (PDK1). PDK1 inhibits PDH thus blocking pyruvate entry into the respiratory Krebs cycle. Pyruvate therefore remains in the cytoplasm where it forms lactate by NADH reduction—the Warburg Effect.

The underlying cause of injured respiration is therefore connected to HIF-1 transactivation of the gene encoding PDK1, which can be considered a gate-keeping enzyme that regulates the flow of pyruvate, a product of glycolysis, into the mitochondria for oxidation. If PDK1 is encoded then pyruvate builds up in the cytoplasm, and the cell is forced to rely on metabolic energy from glycolysis even if oxygen is available.

The successful measurement of gas phase acetaldehyde using a IV-VI semiconductor diode laser, was performed by Kamat et al wherein the laser operated in cw mode with a heat sink cooled to 101 K by a closed-cycle compressor. FIG. 5 shows the spectral region covered by the tuning of this laser, which was near the P-branch of the carbonyl stretch mode of acetaldehyde. FIG. 6 shows an acetaldehyde absorption feature between 1727.05 cm$^{-1}$ and 1727.15 cm$^{-1}$ measured with this laser. The acetaldehyde absorption feature highlighted in the shaded region of FIG. 6 consists of coupled vibrational and rotational modes for the molecule. As shown in FIG. 9, using a 100 meter long optical path length Herriott gas cell a minimum detection limit of 50 ppb with a 10 second sample integration time was demonstrated. The mid-IR instrument described in Kamat et al. operated at cryogenic temperatures, which required a bulky and costly closed-cycle compressor. Smith et al. described the measurement of acetaldehyde using a variation of the mass spectroscopy method, selected ion flow tube (SIFT) MS that removes acetaldehyde's mass interference with carbon dioxide. FIG. 8 from Smith shows measured acetaldehyde concentrations in the headspace of cultured lung cancer cells. In addition, they observed a decrease in pH and a corresponding increase in lactic acid in the cell culture medium. These results were consistent with the Warburg Effect where blockage of pyruvate from entering the respiratory Krebs cycle results in the generation of lactic acid and gas phase acetaldehyde.

Unfortunately there does not exist a sensitive enough, easily portable and cost effective detection mechanism for air-based analytes. The prior art techniques are either not sensitive enough or expensive and bulky, mostly due to the need to provide large bulky compressor or cooling systems. For example, the spectrometer used by Kamat required a closed cycle refrigeration system to cool the system to 101K.

There is a need for a new sensor technology that includes a mid-IR detection device with an improved cooling system which allows for the rapid and cost-effective detection of analytes in gaseous samples, for example at sensitivities that allow for enhanced detection and/or treatments of cancer.

SUMMARY

Before describing several embodiments of the presently described inventive concepts, it is to be understood that the inventive concepts are not limited to the embodiments summarized below. The inventive concepts are capable of other embodiments or of being practiced or carried out in various ways such as are described elsewhere in the present disclosure. As such, the embodiments described in the summary below are meant to be exemplary, not exhaustive.

Embodiments of an apparatus or sensor for detecting analytes (e.g., molecules) in samples such as gaseous or fluid samples are disclosed. In one embodiment the apparatus or sensor can be used for assessing metabolic energy flow material. Methods of fabrication and use of such apparatus are disclosed. Embodiments of a mid-IR detection device with a monolithically integrated cooling portion which can be used in a detection system and/or methods to detect analytes are disclosed. In one embodiment, a metabolic energy flow is assessed. A metabolic energy flow which is associated with the altered metabolism of cancerous cells or tissues can be determined by the measurement of acetaldehyde present in a breath sample taken from a subject or a gaseous sample taken from skin in such a subject, or from another area found in or around cancer cells.

Additional embodiments include new sensor technologies wherein a mid-IR detection device coupled with a monolithically integrated cooling portion allows for the rapid and cost-effective detection of air-based analytes, for example wherein the analytes are biomarkers detectable at sensitivities that allow for enhanced detection and/or treatments of cancer.

In one embodiment, the detection apparatus has a gas-cell, a mid-IR laser, and a mid-IR detection device. The gas-cell defines a detection space, and may be implemented as a long optical path length cell having a path length measuring in meters, for example in one non-limiting embodiment the path length is between 10 m and 200 m. The mid-IR laser is configured to project a beam of electromagnetic energy having an infrared spectrum through at least a portion of the detection space. The mid-IR detection device may be formed of a monolithically integrated crystalline structure comprising a detection portion, a cooling portion and an isolation portion. The detection portion may be configured as a photovoltaic detector and positioned relative to the mid-IR laser to receive at least a portion of the beam of electromagnetic energy. The detection portion generates an electrical signal responsive to receipt of the beam of electromagnetic energy. The cooling portion is configured to receive a stimulus and to actively move thermal energy away from the detection portion with aid of the stimulus. The isolation portion is between the detection portion and the cooling portion, the isolation portion electrically isolates the detection portion from the cooling portion.

Additional features of the embodied detection apparatus may include semiconductor layers, which are lattice matched or substantially lattice matched to each other. The cooling portion can be implemented as a thermoelectric (TE) layer optionally comprising appropriate doping levels to achieve specified electron or hole concentration ranges and wherein the thermal energy is transported in a direction of charge carrier flow. In some embodiments, the TE layer may include IV-VI semiconductor matrix material, which can be a IV-VI semiconductor compound, alloy, or superlattice. Additionally, the matrix material may have a series of quantum well sub-layers comprising a first quantum well sub-layer having a first thickness, and a second quantum well sub-layer having a second thickness. The first quantum well sub-layer is between the detection portion and the second quantum well sub-layer and the first thickness is greater than the second thickness. The quantum well sub-layers may be of various sizes. The different quantum well thicknesses may be arranged such that the first quantum well sub-layer is adjacent to the detection portion, and the second quantum well sub-layer is adjacent to a heat sink bonded to the cooling portion.

In one embodiment, the mid-IR detection device may be fabricated by epitaxially growing a detection device structure including a thermoelectric layer, an isolation layer, and a pn junction layer on a growth substrate. In this non-limiting embodiment an adhesive material may be applied to at least one of a top portion of the detection device structure adjacent to the pn junction layer and a temporary handle substrate and bonding the detection device structure to the temporary handle substrate. The growth substrate is removed, and one or more metal bonding layer is deposited on at least one of an exposed bottom of the detection device structure adjacent to the thermoelectric layer and a surface of a heat sink and bonding the detection device structure to the heat sink. The temporary handle substrate is removed, and a portion of the pn junction layer and the isolation layer is etched to provide access to the thermoelectric layer. A portion of a first sub-layer of the pn junction layer is further etched to provide access to a second sub-layer of the pn junction layer. The first sub-layer comprises a p-type or n-type material, and the second sub-layer comprises a p-type or n-type material that is different from the p-type or n-type material of the first sub-layer. An electrically insulating passivation layer is deposited over the detection device structure, and predetermined portions of the electrically insulating passivation layer are etched through. Then, metal contacts are formed to the first and second sub-layers in the pn junction layer and the thermoelectric layer.

Some embodiments are directed to a method of detecting a presence and/or concentration of an analyte such as but not limited to a biomarker in a gaseous or fluid sample. In one embodiment, the method comprises subjecting the gaseous or fluid sample to laser absorption spectrometry via a tunable laser adsorption spectrometer system that comprises a detection apparatus described in the present disclosure. The gaseous sample can be, for example, a sample of exhaled breath, or may be collected from an atmosphere in proximity to a skin of a patient. The gaseous sample may be an evaporated portion of a liquid sample. The measured analyte may be any analyte which is correlated with the presence of a particular biological condition, disorder, disease, or metabolic state, including but not limited to a cancerous condition.

Another embodiment includes a method for cancer detection or monitoring in an animal such as a mammal by determining an increased accumulation of any analyte which is correlated with a cancerous condition and which is measurable with a mid-IR wavelength using a tunable laser absorption spectrometer system. The tunable laser absorption spectrometer system may include: a mid-IR laser; a gas cell with a vacuum pump; a mid-IR detection device with a monolithically integrated thermoelectric cooling portion; and electronics with user interface. For example, pyruvate concentration can be determined by detecting acetaldehyde in a gas phase (or liquid phase).

Another embodiment described in the present disclosure is a mid-IR detection device comprising a detection portion, a cooling portion, an isolation portion, a first set of electrical contacts, and a second set of electrical contacts. The detection portion is configured as a photovoltaic detector to receive at least a portion of a beam of electromagnetic energy. The detection portion generates electrical energy and thermal energy responsive to receipt of the beam of electromagnetic energy. The cooling portion is configured to receive a stimulus and actively move the thermal energy away from the detection portion with aid of the stimulus. The isolation portion is between the detection portion and the cooling portion. The isolation portion electrically isolates the detection portion from the cooling portion, and wherein the detection portion, the cooling portion and the isolation portion are formed as a monolithically integrated crystalline structure. The first set of electrical contacts is on the detection portion and is configured to receive the electrical energy. The second set of electrical contacts is on the cooling portion and configured to provide the stimulus.

Those skilled in the art will appreciate the scope of the present disclosure and realize additional aspects thereof after reading the followed detailed description of the various embodiments in association with the accompanying drawings.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the present disclosure. Further, in the appended drawings, like or identical reference numerals may be used to identify common or similar elements and not all such elements may be so numbered. The figures are not necessarily to scale and certain features and certain views of the figures may be shown exaggerated in scale or in schematic in the interest of clarity and conciseness.

DETAILED DESCRIPTION

Figure 1:
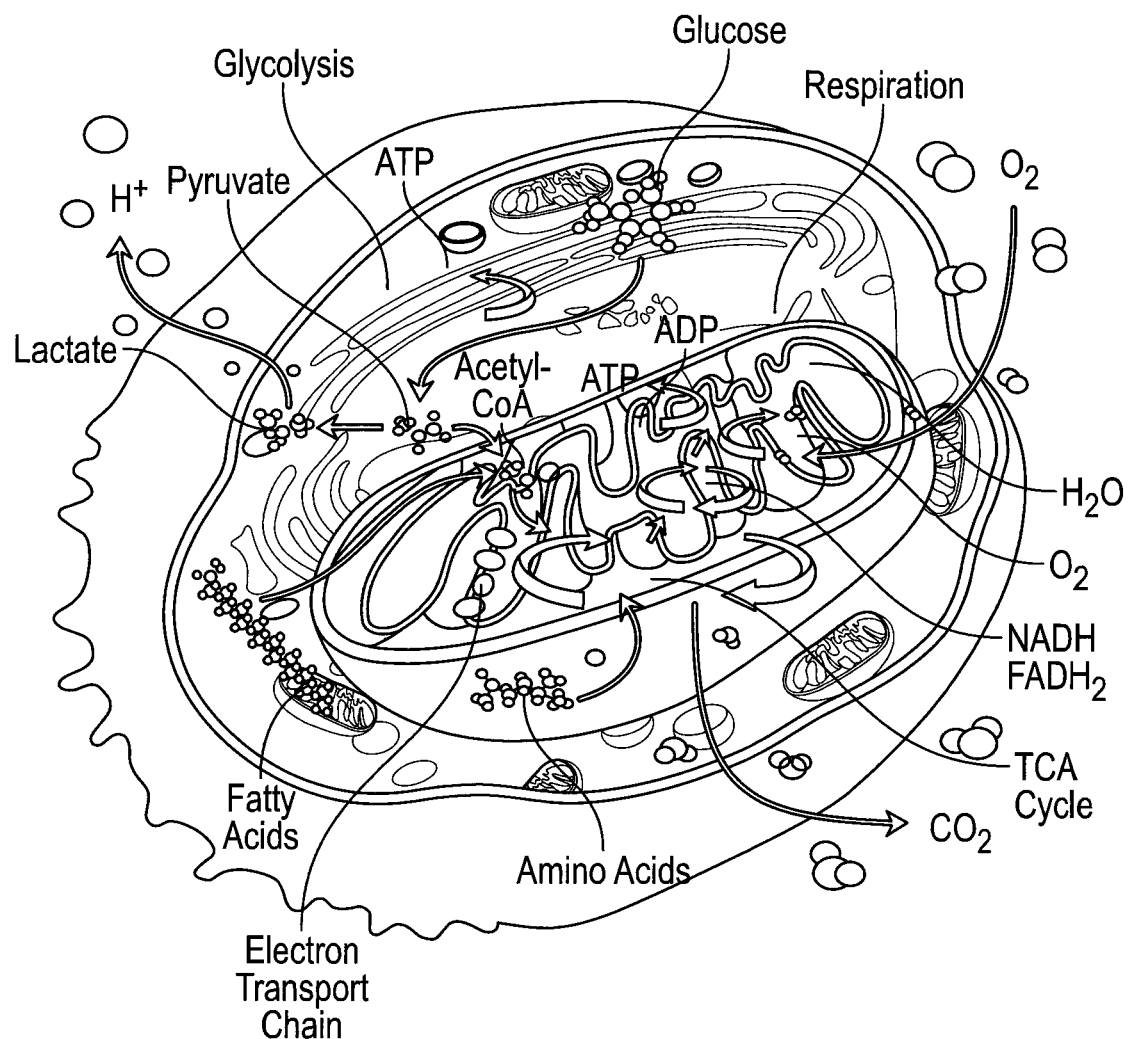
FIG. 1. Depiction of normal cell respiration through the tricarboxylic acid (TCA) (or Krebs) cycle. The first step in pyruvate consumption is transformation to acetyl-CoA by pyruvate dehydrogenase (PDH).
Figure 2:
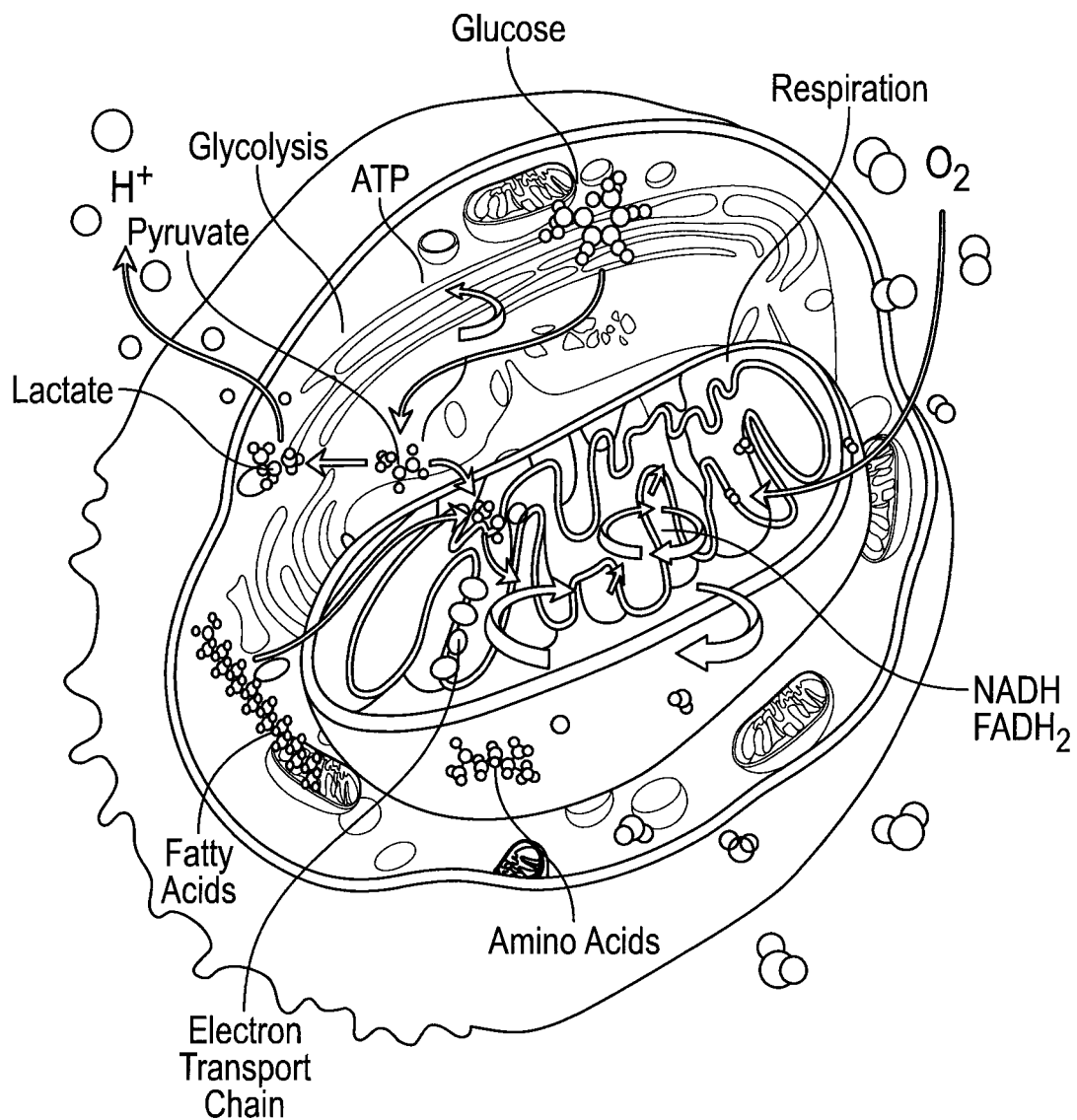
FIG. 2. Depiction of a cell with injured respiration. Cell survival is possible if the glycolysis rate increases to compensate for loss of ATP from injured respiration.

Before explaining the several embodiments of the presently described inventive concepts in detail by way of exemplary drawings, experimentation, results, and laboratory procedures, it is to be understood that the inventive concepts are not limited in its application to the details of construction and the arrangement of the components set forth in the following description or illustrated in the drawings, experimentation and/or results. The inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting.

Unless otherwise defined herein, scientific and technical terms used in connection with the presently disclosed inventive concepts shall have the meanings that are commonly understood by those of ordinary skill in the art. Further, unless otherwise required by context, singular terms shall include pluralities and plural terms shall include the singular. Generally, nomenclatures utilized herein are those well-known and commonly used in the art. The nomenclatures utilized herein are those well-known and commonly used in the art.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the devices, apparatus, and/or methods disclosed herein can be made and executed without undue experimentation in light of the present disclosure. While the components and methods of this disclosure have been described in terms of particular embodiments, it will be apparent to those of skill in the art that variations may be applied to the components and/or methods and in the steps or in the sequence of steps of the methods described herein without departing from the concept, spirit and scope of the disclosure. All such similar substitutes and modifications apparent to those skilled in the art are deemed to be within the spirit, scope and concept of the inventive concepts as disclosed herein.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation or error for the device, the method being employed to determine the value, or the variation that exists among the study objects. The use of the term "at least one" will be understood to include one, as well as any quantity more than one, including, but not limited to, for example, 2, 3, 4, 5, 6, 7, 8, 9, 10, 15, 20, 30, 40, 50, 100, or greater. The term "at least one" may extend up to 100 or 1000 or more, depending on the term to which it is attached; in addition, the quantities of 100/1000 are not to be considered limiting, as higher limits may also produce satisfactory results in certain embodiments. In addition, the use of the term "at least one of X, Y and Z" (where X, Y and Z are intended to represent, for example, three or more objects) will be understood to include X alone, Y alone, and Z alone, as well as any combination of X, Y and Z, such as X and Y, X and Z, or Y and Z.

The term "about" is used to indicate that a value includes the inherent variation or error for the device, the method being employed to determine the value and/or the variation that exists among study items.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

While the presently disclosed inventive concepts will now be described in connection with particular embodiments in the following examples so that aspects thereof may be more fully understood and appreciated, it is not intended to limit the presently disclosed inventive concepts to these particular embodiments. On the contrary, it is intended to cover all alternatives, modifications and equivalents as may be included within the scope of the presently disclosed inventive concepts as described herein. Thus, the following description serves to illustrate the practice of this presently disclosed inventive concepts, it being understood that the particular embodiments shown and discussed are by way of example and for purposes of illustrative discussion of the presently disclosed inventive concepts only and are presented in the cause of providing what is believed to be the most useful and readily understood description of formulation procedures and methods as well as of the principles and conceptual aspects of the presently disclosed inventive concepts.

Disclosed herein are methods of using and fabricating a detection apparatus or sensor which incorporates a mid-IR detection device. In one embodiment, the detection apparatus or sensor can be used to measure analytes (molecules) in gas phase or liquid phase. Such molecules can include organic and inorganic compounds, such as biomarkers. In one embodiment the analytes include acetaldehyde and pyruvate. Solid state cooling of a crystalline lattice is effectively achieved with a controlled flow of charge carriers that absorb thermal energy from the semiconductor material that is designed to sense mid-IR photons. Reduction in temperature improves signal-to-noise ratios thus improving molecular sensitivity. Where used herein the term "mid-IR"

refers to electromagnetic wavelengths in a range of from about 2.4 micrometers to about 12 micrometers.

Determination of an increased accumulation of pyruvate, as described herein, when metabolic energy flow shifts from respiration to aerobic glycolysis is useful in a variety of areas. It is known that aerobic glycolysis accompanies cancerous tumor growth, so determining an increase in pyruvate concentration would indicate altered metabolism and suggest the presence of cancer. A sensor that can determine an increase in pyruvate concentration can be used to detect cancer and monitor a patient's response to cancer therapy. In addition, it can be used to perform in vitro and in vivo measurements to assess the effectiveness of experimental drug compounds that target the aerobic glycolysis metabolic energy flow mechanism that supports the survival and growth of cancer cells. Other applications include but are not limited to the monitoring of anaerobic metabolic energy flow mechanisms such as those that are used in biofuel production.

An embodied method disclosed herein involves but is not limited to the detection of acetaldehyde, a reaction product produced from pyruvate when it loses a carbon dioxide molecule. Equilibrium favors the gas phase existence of acetaldehyde ($C_2OH_4$) at a 37° C. body temperature since it has a boiling point of 20.2° C. This provides an example of a molecule that is suitable for measurement in the gas phase. Based on equilibrium thermodynamics and reaction kinetics, there is a direct relationship between the concentration of pyruvate and the concentration of acetaldehyde. Under steady state conditions, if gas phase acetaldehyde is higher than normal, then it indicates a higher than normal level of pyruvate in the liquid phase. Equilibrium thermodynamics states that the pyruvate to acetaldehyde+$CO_2$ reaction is exothermic releasing 19.8 kJ/mole or 0.21 eV/molecule of energy. At a body temperature of 37° C., at least some acetaldehyde is formed from pyruvate due to equilibrium thermodynamics. The ability to measure trace concentrations (i.e. less than part-per-million levels) of acetaldehyde can be used herein to determine a change in pyruvate concentration and thus an altered metabolism due to cancer.

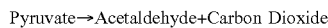

An apparatus that can measure gas phase acetaldehyde, such as is described herein, can therefore be used to determine an abnormally high level of pyruvate in the liquid phase. This can indicate a blockage of pyruvate from entering the Krebs cycle and the aerobic glycolysis metabolic energy flow mechanism that accompanies cancerous cell growth. Acetaldehyde is highly soluble in aqueous solutions, and it diffuses quickly through cell membranes, so its presence in the gas phase can be observed, for example, either in exhaled breath or from the skin in the vicinity of a cancerous tumor. Acetaldehyde formation from pyruvate in biological systems is generally thought to involve catalyzed reactions with the enzyme pyruvate decarboxylase (POC). For example, anaerobic fermentation of glucose with yeast cells involves POC conversion of pyruvate to acetaldehyde, which is followed by conversion to ethanol with alcohol dehydrogenase (NAOH). The enzyme POC is not found in animals, so there is substantially no discussion in the literature about the production of acetaldehyde from pyruvate in animals. Instead, all of the pyruvate resulting from glycolysis is assumed to be converted to lactate through a catalyzed reaction with the enzyme lactate dehydrogenase. Regardless of this lack of discussion in the scientific literature, acetaldehyde, in fact, can be produced from pyruvate, but at a lower rate since it is not a catalyzed reaction and its production will compete with the catalyzed production of lactate.

Figure 3:
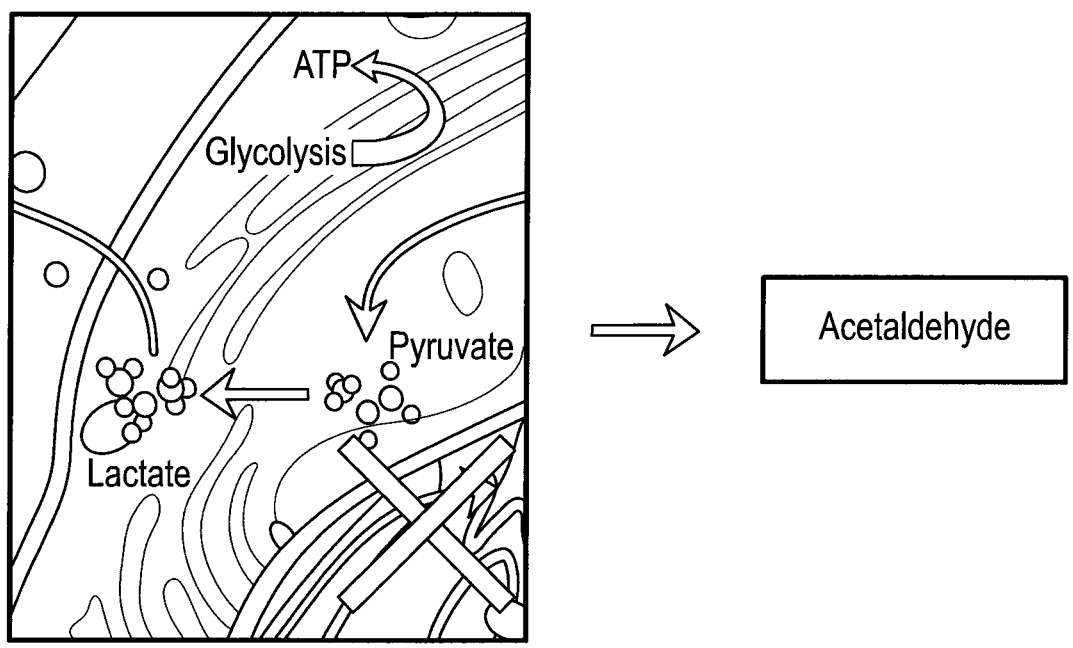
FIG. 3. Depiction of acetaldehyde production from pyruvate. High glycolysis rate and PDK1 blockage of pyruvate from entering the Krebs cycle results in high pyruvate concentrations in cell cytoplasm. Chemical thermodynamics favors formation of acetaldehyde from pyruvate.

FIG. 3 depicts the production of acetaldehyde, an alternative fate for pyruvate following its production from glucose by glycolysis. Acetaldehyde is highly soluble in aqueous solutions, and it has a high vapor pressure (its boiling temperature is 20.2° C.). Its high solubility allows it to diffuse rapidly through cell membranes, and its high vapor pressure favors its existence in the gas phase at a 37° C. body temperature. Detection in the gas phase is therefore one method relied on herein for detection and measurement of acetaldehyde. Prior to the present disclosure there has been technical difficulty in measuring gas phase acetaldehyde. For example, gas chromatography combined with mass spectroscopy (GC-MS), which has been the primary analytical technique for measuring trace gas composition, does not work well in measuring acetaldehyde from biological systems that also produce $CO_2$. This is because both molecules have a molecule mass of 44 grams/mole, so signals for low concentrations of acetaldehyde are obscured by stronger signals for much higher concentrations of $CO_2$. Such analytical difficulties in trace gas measurements in the past may explain why acetaldehyde production from pyruvate has been neglected in the scientific literature.

Although ongoing work with mass spectroscopy may eventually resolve some of the historically conflicting results, the technique will never be suitable for low-cost and easy-to-use point-of-care applications due to the need for bulky vacuum pumps and ultra-high-purity carrier gases. Consequently, there is a need for another technique that can easily and reliably measure sub-ppm concentrations of gas phase acetaldehyde that will also not require bulky components or expensive consumables. Tunable laser absorption spectroscopy (TLAS) is a gas sensing technique that offers these beneficial features.

Tunable laser absorption spectroscopy in embodiments described herein is an alternative analytical technique that can rapidly measure specific gas phase molecules at trace concentration levels (i.e. parts-per-billion). The technique does not suffer from cross species interference problems that make traditional GC-MS ineffective in measuring acetaldehyde. Moreover, tunable laser absorption spectroscopy as described herein does not require pre-concentration of collected gas samples or special high purity carrier gases or any other reagent or consumable. As a result, laser absorption sensors are easy-to-use devices that can measure specific gas phase molecules in real-time at sub-ppm concentrations. This ease-of-use feature enhances the ability to measure gas phase acetaldehyde. Due to its high vapor pressure and its ability to diffuse quickly, acetaldehyde will be present in exhaled breath or in gas samples collected near the skin in the vicinity of its production. If there is increased acetaldehyde production due to a buildup of pyruvate resulting from high glycolysis and low respiration rates—i.e. the Warburg Effect, it will generally be observable in either exhaled breath or near the skin. In accordance with the present disclosure, the measurement of gas phase acetaldehyde from an animal can thus be used to assess metabolic energy flow in that animal. High levels of acetaldehyde in either breath or near the skin indicate a Warburg Effect metabolic state, a condition that accompanies cancer. In addition, gas phase acetaldehyde can be measured from in vitro biological samples such as fluids to assess the metabolic state of that biological system.

Acetaldehyde Measurement with Lasers

Figure 7:
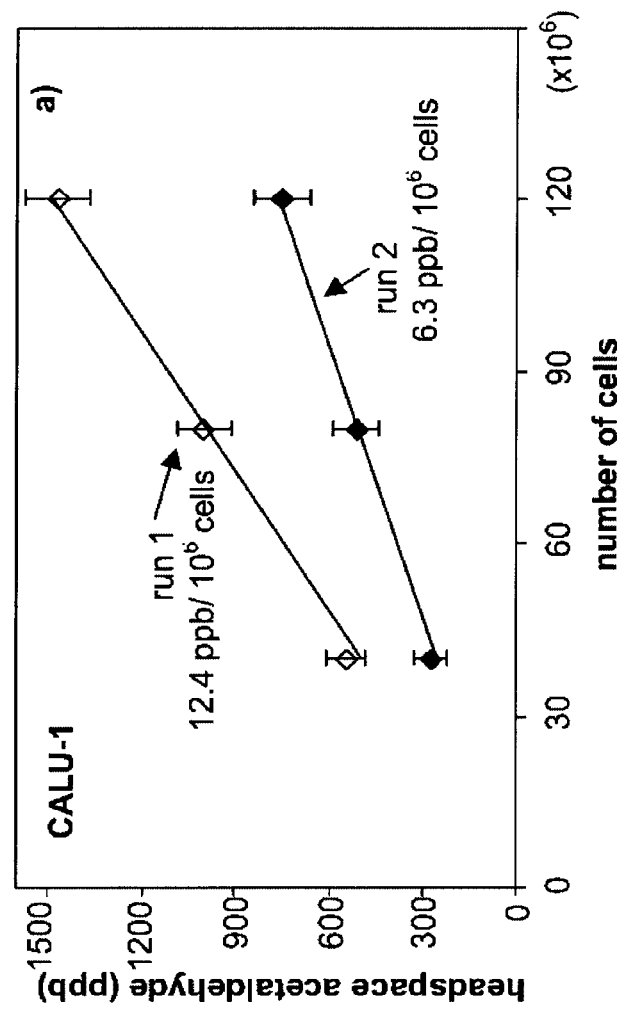
FIG. 7. Graphical depiction of headspace acetaldehyde concentration measured as a function of cultured lung cancer cell quantity.
Figure 8:
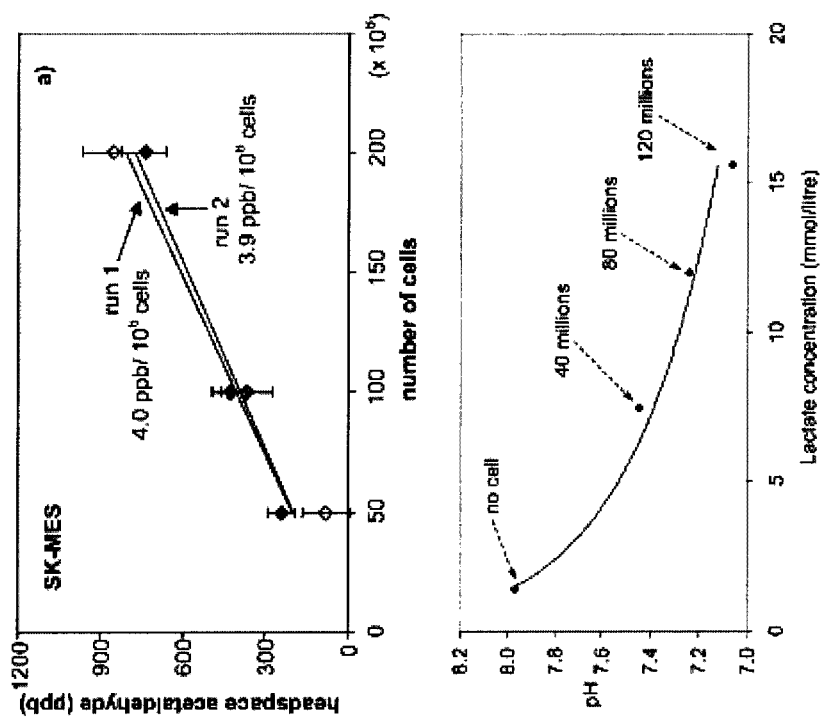
FIG. 8. Graphical depiction of the data from cultured lung carcinoma cell line SK-MES. Top: Headspace acetaldehyde vs. number of cells and Bottom: pH versus lactate concentration and number of cells.

FIG. 7 data shows that the net production of acetaldehyde by cancerous CALU-1 cells is 929 ppb per 10 million cells. A TLAS minimum detection limit of 50 ppb therefore corresponds to 538,000 cells. A tumor containing 0.5 million cells would be about 1 mm in diameter assuming each non-small cell CALU-1 cancer cell is 20 microns in diameter. Such a cancer detection capability exceeds the capability of any known imaging technique thus making a TLAS-based acetaldehyde breath test useful for routine monitoring of cancer occurrence or recurrence or a patient's response to experimental therapies.

Measurement of Exhaled Acetaldehyde

The median exhaled acetaldehyde concentration from healthy adults who have not consumed alcoholic beverages prior to breath sample measurement is about 24 ppb. Observing an increase in exhaled acetaldehyde concentration relative to a baseline reference can be used as part of a protocol for detecting the type of aerobic glycolysis that is uniquely associated with cancer cell metabolism. In one embodiment, the baseline reference can be the 24 ppb concentration established for healthy individuals. Alternatively, a baseline reference can be obtained from the same individual who is being tested. For example, a first acetaldehyde measurement can be conducted after a period of fasting, such as overnight fasting, and then glucose can be administered orally prior to a second exhaled acetaldehyde measurement taken at a later time. In this case the patient serves as their own reference and when an increase in exhaled acetaldehyde is observed then it can be concluded that aerobic glycolysis metabolism is occurring and that cancer cells are present.

Response to Therapy

Measuring gas phase acetaldehyde can be particularly useful when there is a need to monitor a patient's response to therapy. For example, treatment of a tumor with a chemotherapy drug which causes shrinkage of the tumor will result in fewer cancer cells, and thus less metabolic energy being produced by glycolysis, leading to less pyruvate production, and thus less gas phase acetaldehyde. Detection of a decrease in gas phase acetaldehyde would therefore indicate a successful response to the drug protocol. Alternatively, absence of a decrease in gas phase acetaldehyde during therapeutic treatment would indicate that the treatment was not effective and would indicate a change in therapy. This type of patient monitoring, which is extremely easy to perform, helps care providers develop, tailor, or alter drug protocols more quickly. Treatment with more effective therapies earlier in the progression of the disease will help increase the survival rates of cancer patients.

Early Cancer Detection

Screening individuals for gas phase acetaldehyde can also be used to detect cancer at its earliest stages. In this case, an increase in gas phase acetaldehyde concentration relative to a baseline (e.g., based on an individual measurement or a baseline level established from a population, such as 24 ppb) level indicates an increase in pyruvate accumulation and the shift of metabolic energy flow from respiration to glycolysis. In one embodiment, an early cancer detection protocol can involve routine periodic (e.g., daily, weekly, biweekly, monthly, bimonthly, semi-yearly, yearly) measurement of gas phase acetaldehyde in exhaled breath samples. If a sustained increase is observed over time in exhaled breath samples, then attempts can be made to locate the site of acetaldehyde production by measuring gas samples collected from the surface of the skin. For example, an ovarian cancer tumor with an altered metabolic energy flow will have accumulating pyruvate thus producing acetaldehyde that can diffuse through the skin. Observation of higher gas phase acetaldehyde concentrations above the skin in the vicinity of the lower abdomen can indicate the presence of a growing ovarian tumor. This type of cancer detection can be particularly useful for improving survival rates since techniques are not presently available to perform early detection for diseases like ovarian cancer.

Use in Research

Ability to also measure trace concentrations of gas phase acetaldehyde will facilitate biomedical research. As described above, an increase in acetaldehyde concentration can indicate an increase in the accumulation of pyruvate in a biological system. Acetaldehyde is also a suspected signaling molecule. Its ability to diffuse rapidly though biological tissue means that it can trigger specific responses by cells that are distant from the original source of acetaldehyde production such as from a pyruvate overflow effect caused by injured respiration. It is this type of signaling that can contribute to cancer metastasis as described by Hsiang et al. [5]. Measuring acetaldehyde will facilitate research into the possible role of this molecule in the signaling of various biological responses. Measurements can be performed with either in vitro or in vivo biological systems.

Modern biofuel production involves anaerobic fermentation to produce ethanol where acetaldehyde is an intermediate metabolite produced from pyruvate. In contrast to animal metabolism where acetaldehyde concentrations are expected to be small due to the absence of pyruvate decarboxylase (POC), much larger concentrations of acetaldehyde are expected in ethanol production. Selective detection of acetaldehyde concentrations in the gas phase can facilitate optimization of fermentation conditions to improve the efficiency of biofuel production.

Drug Discovery, Development, Clinical Trials, and Personalized Medicine

Renewed interest in the Warburg Effect has recently inspired efforts to develop new pharmaceutical compounds that target specific steps in the metabolic energy flow pathway that supports cancerous cells. Compounds that can restore respiration and reduce the rate of glycolysis can starve cancer cells of energy and help reduce and eliminate tumors. A tool that can monitor cell metabolism in real time offers great value in the effort to expedite the testing of these experimental compounds. For example, Seahorse Bioscience (North Billerica, Mass.), has developed an instrument that measures oxygen consumption rate (OCR) and extracellular acidification rate (ECAR), which is an indicator of lactic acid increase from pyruvate accumulation. Using fluorophore sensors immersed in the liquid solution above a cell culture, this instrument provides information on metabolic energy flow, i.e. how much is Krebs cycle respiration and how much is aerobic glycolysis. The measurements that these instruments perform provide valuable data that create a better understanding of and can be used to develop innovative therapies for a variety of conditions that include heart disease, diabetes, and cancer.

In another embodiment, trace gases can be measured in the headspace above cultured cells using the embodied techniques and mid-IR technologies described herein. Acetaldehyde is among the molecules expected in such gas phase samples. An increasing concentration of vapor phase acetaldehyde would indicate an increasing concentration of pyruvate. This observation, especially if a reduction in oxygen consumption occurs at the same time, can indicate injured respiration and an increasing rate of aerobic glycolysis. Such an acetaldehyde measurement would provide the same information as an ECAR measurement. But in this case the parameter being measured is more specific to metabolic energy flow since it directly originates from an intermediate metabolite, pyruvate. The ECAR parameter is less specific since other factors besides an increase in lactic acid can cause an increase in acidification rate. Furthermore, analyzing headspace gas samples is technologically easier since there is no need to immerse a transducer into the liquid cell culture medium.

A further advantage of a simple and non-intrusive way to collect data that can accurately determine metabolic energy flow pathway such as the embodied methods described herein is in the on-line monitoring of biological systems. This capability improves the speed of research because real-time data can be collected to assess more quickly the results of an experiment. It will therefore expedite drug discovery and facilitate drug development. Ultimately, the same easy sample collection feature involved with gas phase acetaldehyde measurement can also be used to monitor animals and humans during clinical trials. For example, the effectiveness of an experimental lung cancer drug that targets the metabolic energy flow mechanism can be assessed on each participant with a simple-to-perform breath test. If acetaldehyde concentration decreases relative to a baseline measurement before treatment, then it can be concluded that the treatment is effective for that individual. On the other hand, if acetaldehyde does not decrease for an individual following treatment, then it can be concluded that the experimental treatment is not effective for that individual. Such participant monitoring can help improve clinical trials since non-responsive individuals can be excluded from participation.

A long-term outcome of assessing an individual's real-time metabolic response to an experimental therapy is that treatment can be tailored to each individual. A test that measures gas phase acetaldehyde, which is easy to perform and provides immediate results, will enable much faster determination of an effective treatment for the disease that is being treated. This new metabolic energy flow test combined with a variety of potentially effective treatments will result in a new era of personalized medicine where different disease phenotypes are treated with appropriately tailored drugs.

Figure 4:
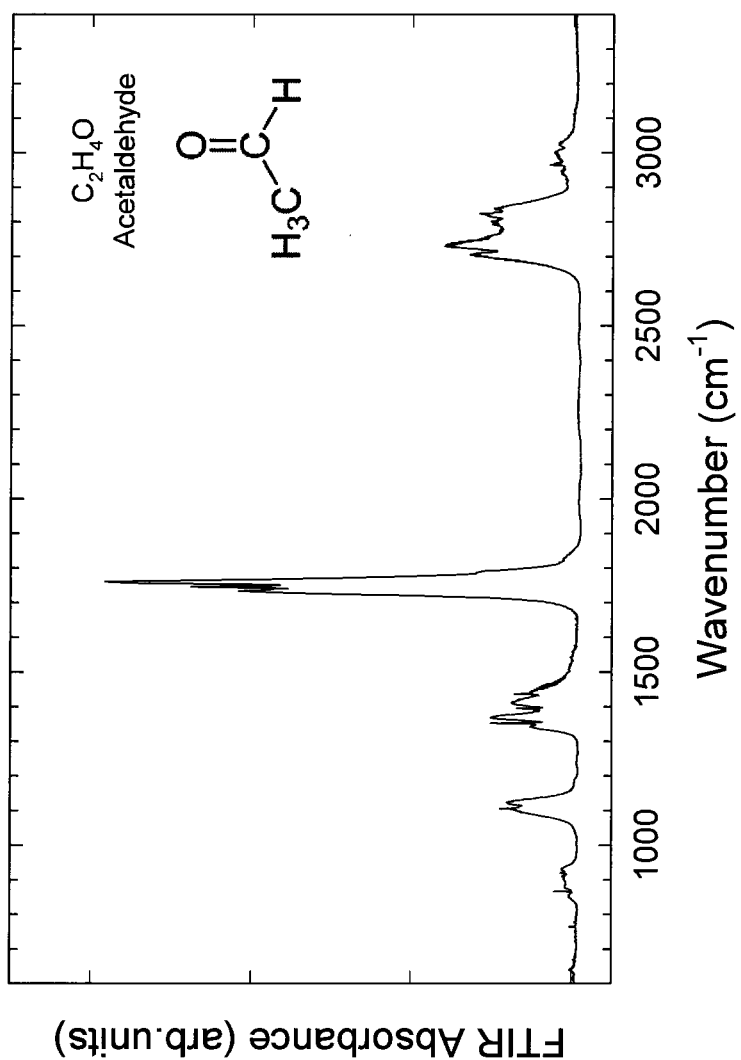
FIG. 4. Graphical depiction of the absorption spectrum for gas phase acetaldehyde as measured by low spectral resolution (0.5 $cm^{-1}$) Fourier transform infrared (FTIR) spectroscopy.
Figure 5:
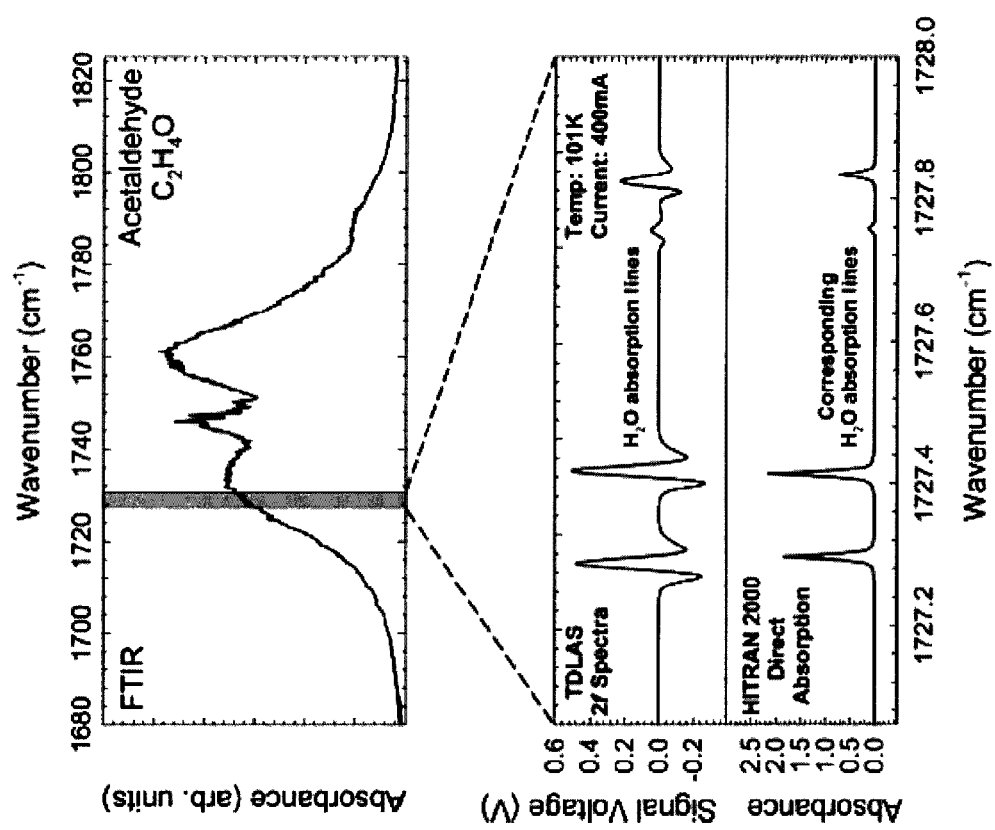
FIG. 5. Upper graph: FTIR absorption spectrum of acetaldehyde. Lower graphs: TLS second harmonic absorption spectra showing measured water absorption lines and simulated Hitran database water lines.
Figure 6:
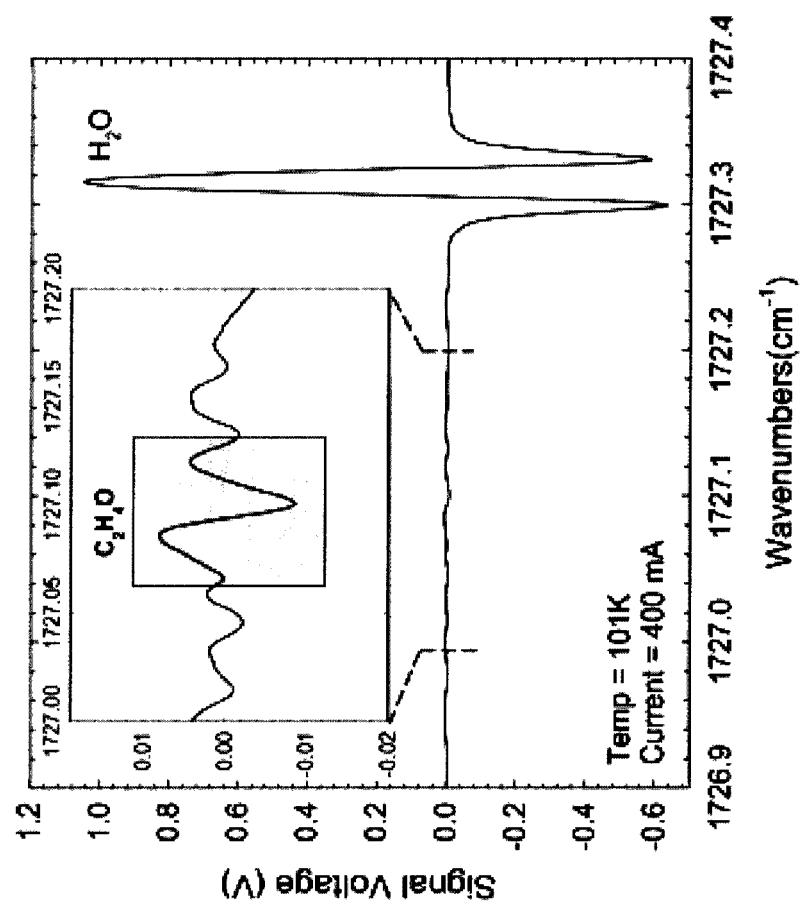
FIG. 6. Graphical depiction of acetaldehyde infrared absorption in the P-branch of the carbonyl stretch mode (shown in the gray shaded region) that was used to perform real time measurements down to 50 ppb concentrations.

As described above herein, industry-standard GC-MS instrumentation is limited in its ability to measure trace levels of acetaldehyde from biological samples due to mass interference with $CO_2$. Other analytical techniques are therefore required to allow accurate detection of this very useful biomarker molecule. Furthermore, it is desirable to have a measurement technique that does not involve use of reagent chemicals or other consumables that would introduce complications in the operation of the sensor instrumentation. Laser absorption spectroscopy offers all of these beneficial features. The technique of the present disclosure relies on the transmission of tunable infrared laser radiation through a gas sample and detection of the transmitted light intensity with an infrared detector. Different gas phase molecules will absorb electromagnetic radiation at different light frequencies due to their unique vibrational and rotational mode spectra. Laser absorption spectroscopy has very high specificity when measuring gas phase molecules because lasers emit monochromatic radiation with spectral linewidths of typically less than 0.001 $cm^{-1}$. Interestingly, tunable laser spectroscopy (TLS) may in fact mimic the mechanism by which the sense of olfaction operates where neural signaling is prompted by vibrational assistance of electron transport. FIG. 4 shows the infrared absorption spectrum for gas phase acetaldehyde. The strongest absorption bands are the carbonyl stretch mode near 1750 $cm^{-1}$ (5.7 μm) and the carbon-hydrogen (C—H) stretch mode near 2750 $cm^{-1}$ (3.6 μm), Both stretch modes may be used in TLS systems of the embodied disclosure. The highlighted technology in manufacturing a TLS system that can measure gas phase acetaldehyde is the mid-infrared (mid-IR) laser that is required to excite the vibrational mode of the molecule. Three different mid-IR laser technologies are available for accomplishing this task, quantum cascade lasers (QCLs), interband cascade lasers (ICLs), and IV-VI semiconductor diode lasers. Examples are provided below on how each of these mid-IR laser technologies can be used to manufacture an embodied TLS system which is designed to measure a gas biomarker, such as acetaldehyde, and thus assess metabolic energy flow in biological systems.

Embodied Laser Technologies

1. QCL Technology

Commercial availability of QCL technology enables their use in TLS systems that can measure gas phase acetaldehyde. Prospective customers of such an apparatus include, for example, biomedical researchers in industry, academia, and government research laboratories. The primary components of a QCL-base TLS system are a QCL, high heat load heat sink mount, a long optical path length gas cell, and a mid-IR detection device. For example, McManus et al. [**15] described a pulsed QCL TLS system that did not use any cryogenic optoelectronic devices. Both the mid-IR QCL and the mid-IR photovoltaic detector were cooled with compact thermoelectric cooling modules. Subsequent work by this same team at Aerodyne, Inc., resulted in a continuous wave (cw) QCL TLS system. QCL operation under cw conditions, which are desired of the most sensitive molecular detection, was achieved with closed cycle water chilling of the QCL heat sink mount.

QCLs with cw emission in the region of the carbonyl stretch mode of acetaldehyde (1750 $cm^{-1}$) are commercially available. For example, Alpes Lasers offers a QCL that operates in cw mode at a heat sink between −30° C. and −20° C. with a 10 volt bias and >500 mA injection current. The high heat load, >5 watts, often necessitates water-cooling of a high heat load heat sink as was done by the Aerodyne team. Although a QCL TLS system can be designed and built for gas phase acetaldehyde detection, the high power input and high waste heat load from the compact laser package create thermal management problems that will inhibit the reduction in size and cost of such instruments. For comparison, the laser in a DVD player typically dissipates less than 50 mW of heat during operation, a 100 times less than a QCL, and this is a much easier thermal management problem to solve.

2. ICL Technology

ICLs represent another class of cascade laser technology. Due to a fundamentally different mechanism of light generation, ICLs require much less voltage and can be operated with much smaller injection currents. The reduction in power consumption and waste heat generation as compared to QCLs is significant. For example, ICLs with power input levels of less than 30 mW, comparable to the DVD lasers discussed above, have been demonstrated. In addition, recent work has shown that these mid-IR lasers can operate in cw mode with heat sinks that are well above room temperature. With low power consumption, low waste heat, and room temperature cw operation, ICLs offer great promise for the fabrication of compact TLS systems for trace gas measurements. A recent demonstration of an ICL with an emission wavelength of 10.4 mm (962 cm$^{-1}$) at a heat sink temperature of 160 K provides an approach to achieve this objective.

3. IV-VI Semiconductor Diode Lasers

IV-VI semiconductor diode lasers typically have very low power consumption and low waste heat, similar to ICLs. But commercially available devices, which can be used to excite the strongest carbonyl stretch vibrational mode of acetaldehyde, require cryogenic cooling for cw operation. IV-VI semiconductor diode lasers that can be operated in cw mode near or at room temperature which use epitaxial material packaging methods that increase significantly the dissipation of heat from the laser active region can be used in the disclosed embodiments. Molecular beam epitaxial (MBE) growth and processing of IV-VI semiconductor material for mid-IR laser fabrication is an active area of research and development. Recent advances include the growth of high crystalline quality p-n junction double heterostructure laser structures on industry-standard silicon wafers and transfer of these epitaxial materials to high thermal conductivity heat sinks which will provide fabrication of tunable mid-IR lasers that have low power consumption, low waste heat generation, and higher cw operating temperatures. In this mid-IR laser technology there is no need for sub-nanometer layer thickness precision, and the MBE growth substrates are relatively inexpensive.

4. Gas Phase Biomarkers

The data in FIG. 7 show that 5 million lung cancer cells produce acetaldehyde concentrations between 30 and 60 ppb, which is in the range of the demonstrated minimum detection limit with the laser absorption spectroscopy method described herein. A tumor containing 5 million cancer cells, assuming each cell is 10 μm across, would have a diameter of less than 2 mm. This tumor size is below the detection limit of even the best x-ray or magnetic resonance imaging technologies. The ability to detect such a small tumor based on a simple breath test represents a significant advance in cancer detection and the ability to treat cancer patients more effectively.

Figure 10:
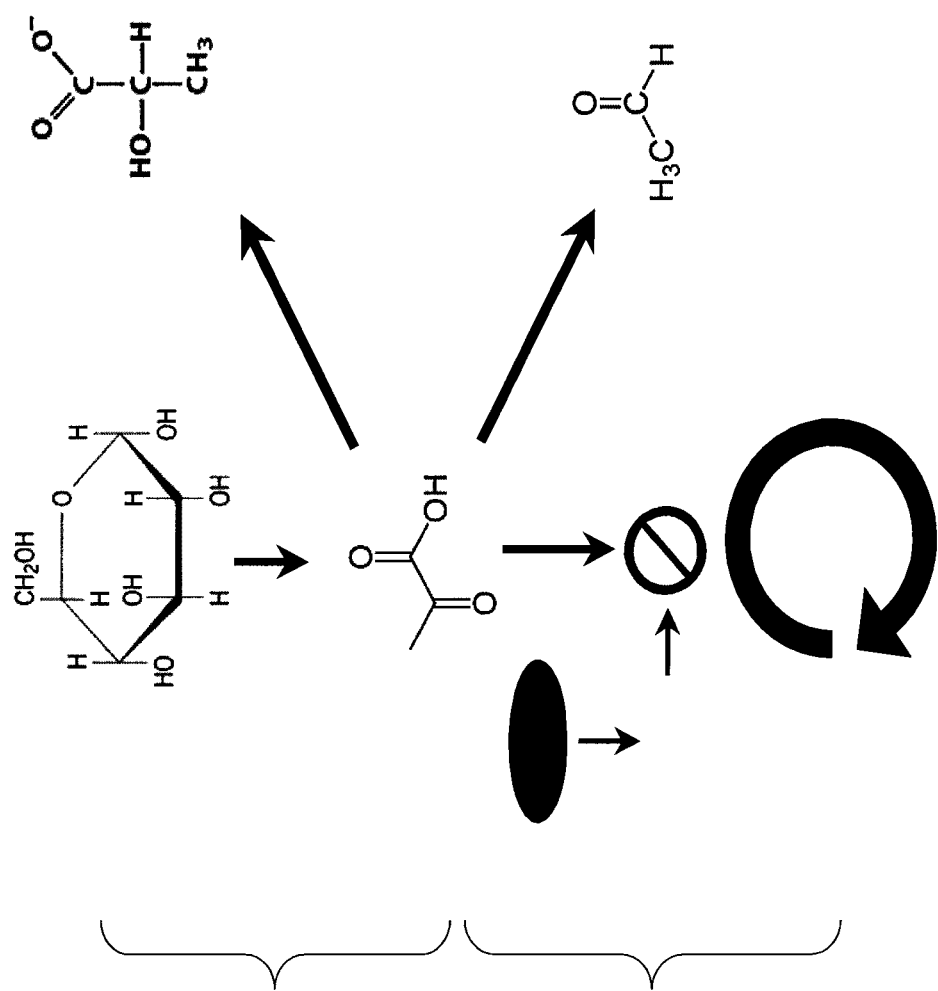
FIG. 10. Depiction of the altered metabolism in cancer cells (Warburg Effect). HIF-1 (hypoxia inducible factor) expression blocks pyruvate entry into the respiratory Krebs cycle.

In cancer cells it is known that blockage of pyruvate from entering the Krebs cycle is responsible for injured respiration (i.e. the Warburg effect). Under Warburg effect conditions the cellular microenvironment will therefore have an elevated pyruvate concentration. Two other pathways for pyruvate processing are summarized in FIG. 10. In cancerous cells pyruvate can form lactate, as observed by Warburg, or it can degrade to acetaldehyde and carbon dioxide. Observing an increase in gas phase acetaldehyde can thus indicate an increased pyruvate concentration. Acetaldehyde is therefore a gas phase biomarker for detection of cancer.

The gaseous sample analyzed using the present methods may be an evaporated portion of a liquid sample. The measured analyte may be any analyte which is correlated with the presence of a particular biological condition, disorder, disease, or metabolic state, including but not limited to a cancerous condition. Certain embodiments disclosed herein are designed to measure gas phase (or liquid phase) analytes such as molecules which are biomarkers of the preexisting biological condition, disorder, disease, or metabolic state. In one embodiment the biomarker is acetaldehyde, such as is produced when Warburg effect conditions are present. Such measurements will greatly facilitate discovery of novel therapies such as cancer therapies, especially those that target the altered metabolism of cancerous cells. The embodied technology can be used to perform basic cancer research, identify effective pharmaceutical therapies more quickly, facilitate animal and human monitoring during clinical trials, assess patient response to cancer treatment, and be used to detect cancer at stages earlier than previously possible.

5. Optical Absorption Spectrometers

Figure 9:
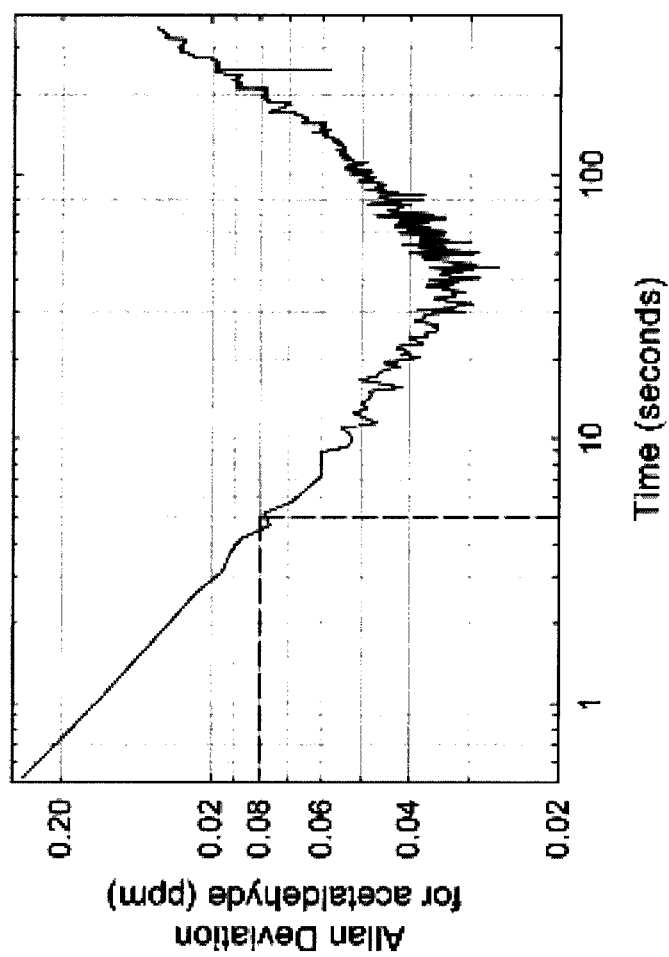
FIG. 9. Graphical depiction of the minimum acetaldehyde detection limit as a function of electronics integration time.

Optical absorption spectroscopy with tunable mid-IR lasers is a technology that mimics biological olfactory sensing. In an optical absorption spectrometer an electrically-controlled optical field excites molecular rotational-vibrational modes. A mid-IR detection device, arranged to measure the intensity of transmitted light through a gas cell, provides a signal from which both the concentration and the specific identity of a molecular compound can be determined. The technology offers the advantages of fast detection and excellent sensitivity with a non-contact method that allows reliable detection of reactive or unstable molecules. Recent work with mid-IR diode lasers has shown that a large variety of molecules can be measured in real time with ppb sensitivities, a sensitivity range that rivals canine capabilities. For example, previous work has shown a tunable laser absorption spectroscopy measurement of exhaled acetaldehyde with a minimum detection limit of 50 ppb, see FIG. 9.

Interband cascade lasers (ICLs) have been used to demonstrate a lack of methane on Mars with a 1.3 ppb minimum detection limit. Such devices can be operated at room temperature with low power consumption. However, without the novel improvements in mid-IR detection described herein, the costs of laser-based sensors using ICL technology remains too high thus limiting their potential usefulness and impact. The embodiments disclosed herein cover a new mid-IR detection device technology that enables the development of low cost gas sensors. By providing an active cooling system within close proximity to the mid-IR photon detection portion, this technology enables the fabrication of compact and low cost mid-IR detection devices having the performance capability for sub-ppb minimum detection limits.

Good sensor sensitivity requires large signal-to-noise ratios coming from the detecting element that provides the electrical signal. This is the case in both biological olfactory sensing and in the solid state detecting element described below. Thermal effects are responsible for much of the electronic noise in these detecting elements, so cooling is a fundamental way to improve detection sensitivity and achieve low minimum detection limits. In one embodiment, the presently disclosed detection apparatus combines a mid-IR photovoltaic detection portion in close proximity to a cooling portion. For example the mid-IR photovoltaic detection portion and the cooling portion are within the same crystalline structure thus making possible monolithic integration of an actively cooled mid-IR photovoltaic detector.

6. Embodied Mid-IR Detection Devices

Figure 11:
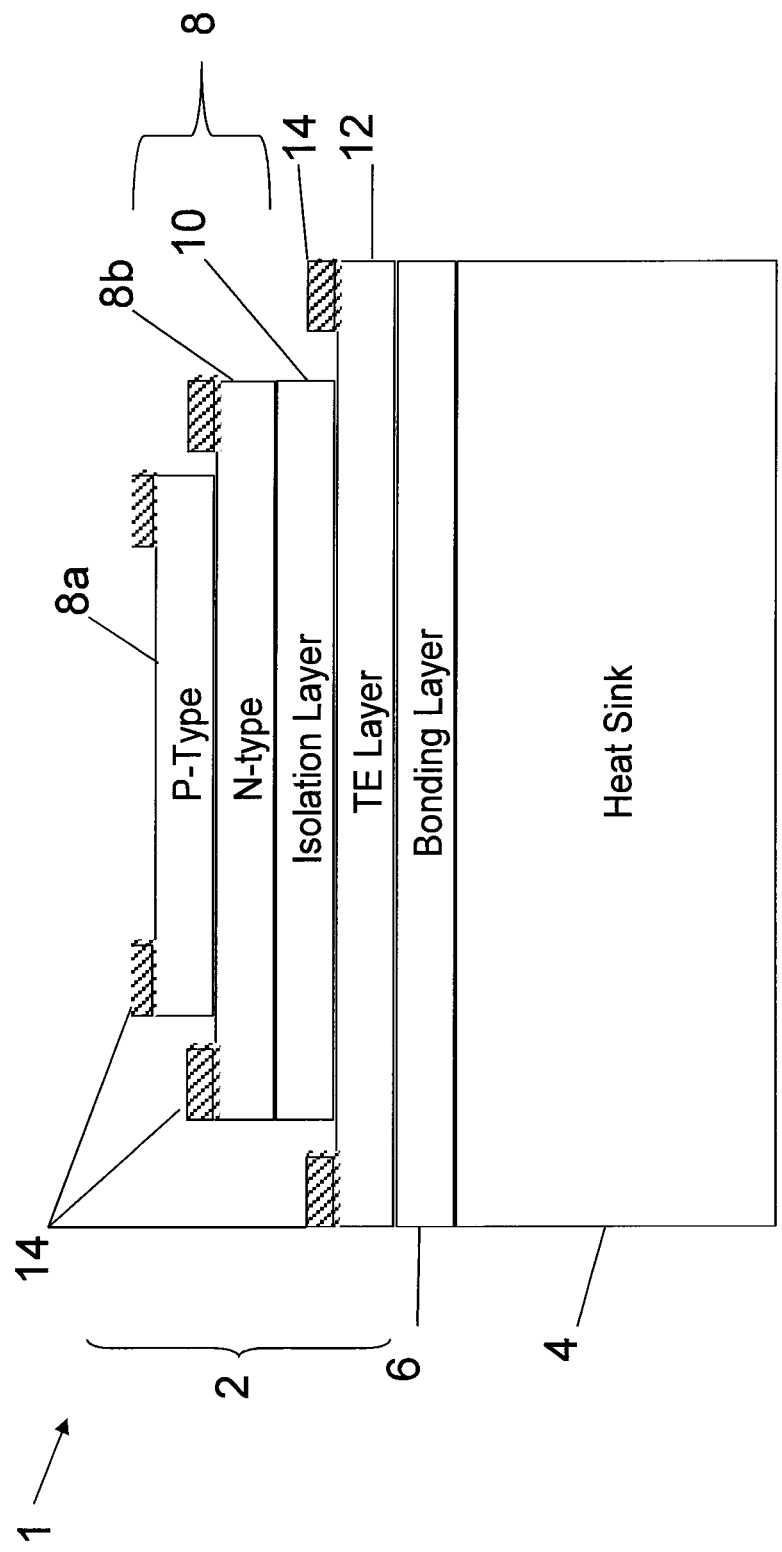
FIG. 11. A cross-sectional drawing of an embodied mid-IR detection device with a monolithically integrated cooling portion.

Non-limiting examples of mid-IR detection devices of several embodiments of the present disclosure are described below. FIG. 11 shows a cross sectional drawing of an embodied mid-IR photovoltaic sensor 1 including a mid-IR detection device 2 and a heat sink 4. The mid-IR detection device 2, which is bonded to the heat sink 4 with an electrically and thermally conducting bonding layer 6, is comprised of multiple layers, which are formed as a monolithically integrated crystalline structure that can be grown using techniques, such as molecular beam epitaxy (MBE) or metal organic vapour phase epitaxy (MOCVD). The layers include a detection portion 8, that can be implemented as one or more p-type layers 8a and one or more n-type layers 8b which form a photovoltaic pn junction mid-IR light detection structure. Although the p-type layer 8a is shown on top of the n-type layer 8b, it should be understood that this can be reversed. The mid-IR detection device 2 is also provided with an isolation portion 10 which can be formed of one or more electrical isolation layer, and a cooling portion 12 which may be implemented as a thermoelectric (TE) layer. Four independent electrical contacts 14 are provided to the n-type layer 8b, p-type layer 8a, and the top and bottom of cooling portion 12, where the heat sink 4 can be constructed of an electrically conductive material, such as copper or aluminum, and form a bottom contact of the cooling portion 12 via the electrically and thermally conducting bonding layer 6. For example, one or more electrical contacts may also be positioned on the heat sink 4 to allow current to be flowed through the TE layer. (electrical contacts 14 are not shown on the heat sink). The electrical contacts 14 to either side of the pn junction 8 provide photovoltage signals that are proportional to the intensity of absorbed mid-IR light, while the electrical contacts 14 to the cooling portion 12 are used to receive a stimulus, such as electrical potential, and thereby flow electrical current through the cooling portion 12 to actively move thermal energy away from the detection portion 8. The isolation portion 10 provides electrical insulation between the cooling portion 12 and the detection portion 8, and can be constructed of one or more undoped semiconductor layers.

In some embodiments, the detection portion 8 includes a mid-IR sensitive pn junction that can be made from a narrow bandgap IV-VI semiconductor compound or alloy such as PbSe, PbTe, PbSnSe, or PbSnSeTe. Impurities such as bismuth and silver, introduced during MBE growth, can be used to obtain the needed n-type layer 8b and p-type layer 8a layers. The isolation portion 10 can be composed of a larger bandgap IV-VI semiconductor alloy such as PbSrSe or PbSrSeTe that is grown without intentional doping. The cooling portion 12 can also be composed of a IV-VI semiconductor material. The layers forming the detection portion 8, cooling portion 12 and isolation portion 10 can be grown during a single MBE procedure where the IV-VI semiconductor layers are lattice matched or substantially lattice matched to each other, wherein substantially lattice matched means that the lattices have a mismatch of 2% or less. The general procedures for growth and processing of IV-VI semiconductor structures are well known and have been described in the scientific literature.

Active cooling of the detection portion 8 occurs when charge carriers flow through the cooling portion 12. With appropriate doping levels to achieve electron or hole concentrations in the range of $1 \times 10^{18}$ cm$^{-3}$ to $1 \times 10^{19}$ cm$^{-3}$, or in a narrower range of $2 \times 10^{18}$ cm$^{-3}$ to $4 \times 10^{18}$ cm$^{-3}$, thermal energy is transported in the direction of charge carrier flow to the heat sink 4. To achieve an effective heat transport and cooling function, it is helpful for the cooling portion 12 to be made of semiconductor material having a low thermal conductivity. For example, the cooling portion 12 can be constructed of IV-VI semiconductor layers 20 composed of a series of quantum wells fabricated to produce a superlattice structure that has low cross-plane thermal conductivity. The thermal conductivity reduction may be preserved at low temperatures, which is a desirable property for active cooling applications. These superlattice structures may block phonon transport but can still allow easy flow of heat carrying electrons or holes. In this case the charge carriers travel within sub-bands that are formed by quantum wells 22 within the superlattice structure.

Figure 12:
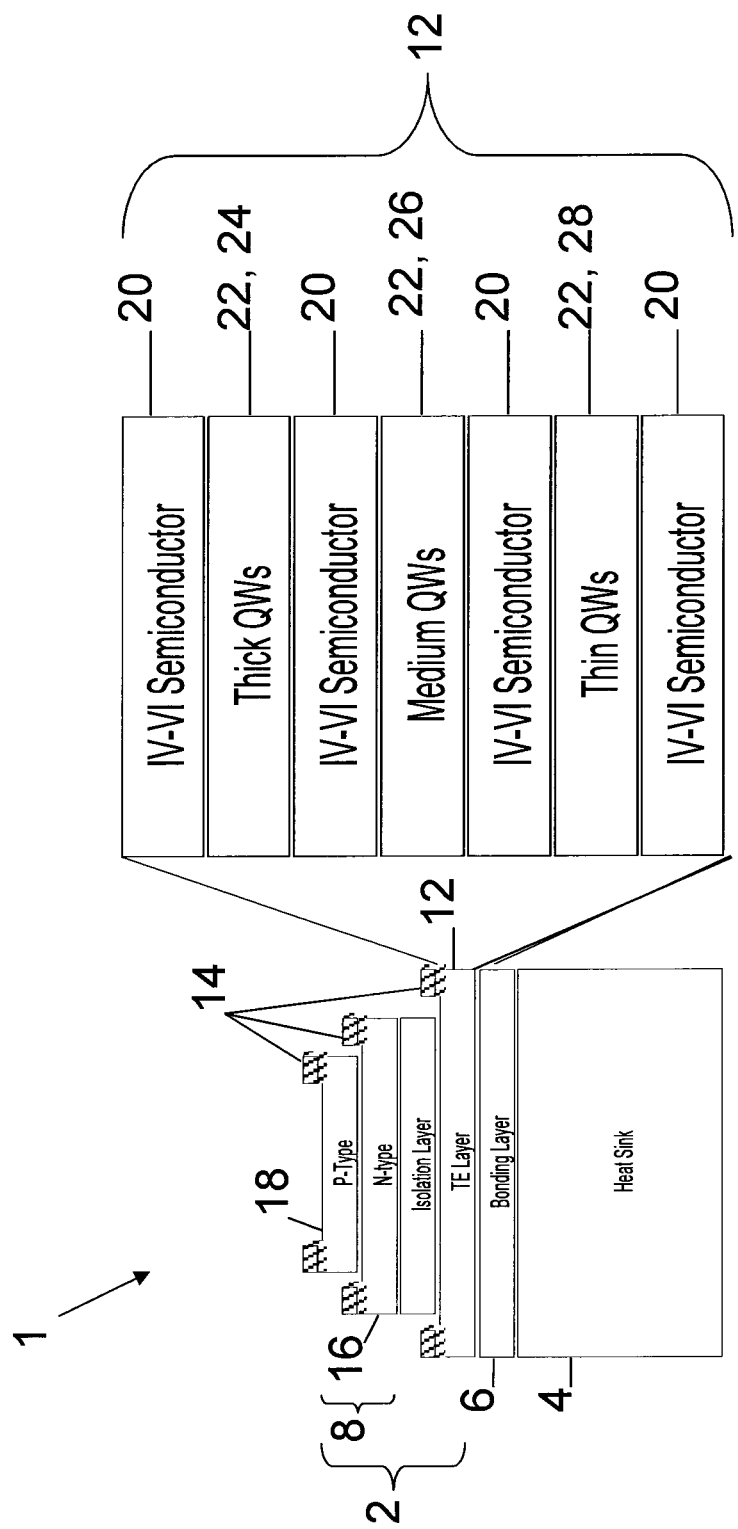
FIG. 12. A cross-sectional drawing of the embodied mid-IR detection device showing embodied structure of the TE layer that is to be used to cool a mid-IR photovoltaic detector.

FIG. 12 shows another embodied design for the structure of the cooling portion 12 that is to be used to cool the detection portion 8, such as a mid-IR photovoltaic detector. The cooling portion 12 includes a IV-VI semiconductor matrix material, which can be a IV-VI semiconductor compound, alloy, or superlattice. Within this matrix material is a series of layers within which are quantum wells 22. Different layers with different quantum well thicknesses are arranged such that a layer with thick quantum wells 24 (e.g., 7-10 nm thickness) is close to the detection portion 8, while a layer with thin quantum wells 28 (e.g., 1-4 nm thickness) is close to the heat sink 4. In between these the layer 20 with thick quantum wells 24 and the layer 20 with the thin quantum wells 28, can be layers 20 with quantum wells 26 that have thicknesses (e.g., 4-7 nm thickness) between those of the quantum wells 24 and quantum wells 28. Thinner quantum wells 28 create higher energy sub-bands for charge carriers, while thicker quantum wells 24 create lower energy sub-bands for charge carriers. This arrangement of quantum well layers 22 is beneficial for active cooling because only the hotter charge carriers with sufficient thermal energy to overcome the potential barriers created by the quantum well (QW) layers 22 will be transported through the cooling portion 12. The charge carriers left behind will thus have a lower collective temperature. The sequence of QW layers 22 described herein will progressively cool the charge carriers to a low temperature thus maintaining a low temperature for the detection portion 8, e.g., the pn junction mid-IR photodetector that is adjacent to and electrically isolate from the cooling portion 12.

The quantum well 22 material can be comprised of PbSe wells surrounded by larger bandgap PbSrSe. Alternatively, it can be comprised of PbSnSe wells surrounded by larger bandgap PbSe. In one embodiment, the thicknesses of the PbSe or PbSnSe quantum wells 22 are in a range of about 1 nm to about 10 nm, a thickness range at which reduction in cross plane thermal conductivity is observed. Quantum size effects cause sub-band energies in thinner QWs 28 to be larger than sub-band energies in thicker QWs 24. The thicker QWs 24 near the detection portion 8 will thus provide a lower energy barrier to charge carrier flow, while the thinner QWs 28 near the heat sink 4 provide a taller energy barrier to charge carrier flow. These barriers will selectively allow "hotter" charge carriers to carry thermal energy to the heat sink 4. This thermionic emission effect is known to enhance the Seebeck coefficient in thermoelectric materials. Typical thermal energies for "hot" charge carriers are in the range of 2-3 times kT, where k is Boltzmann's constant and T is temperature in Kelvins. A barrier for pumping heat near room temperature (e.g., between about 65° F. and about 85° F.) should thus be in the range of about 50 meV to about 75 meV tall. Such barrier heights can be achieved with PbSrSe/PbSe/PbSrSe QWs 22 when the PbSe QW thickness is in a range of, for example, about 2 nm to about 6 nm. A barrier for effective electronic heat pumping at 150 K is, in one embodiment, in the range of about 25 meV to about 38 meV tall. This can be achieved with PbSe/PbSnSe/PbSe QWs 22 when the PbSnSe QW thickness is in a range of, for example, about 5 nm to about 9 nm. This is for the case when the tin content in the PbSnSe alloy is about 15%.

Figure 13:
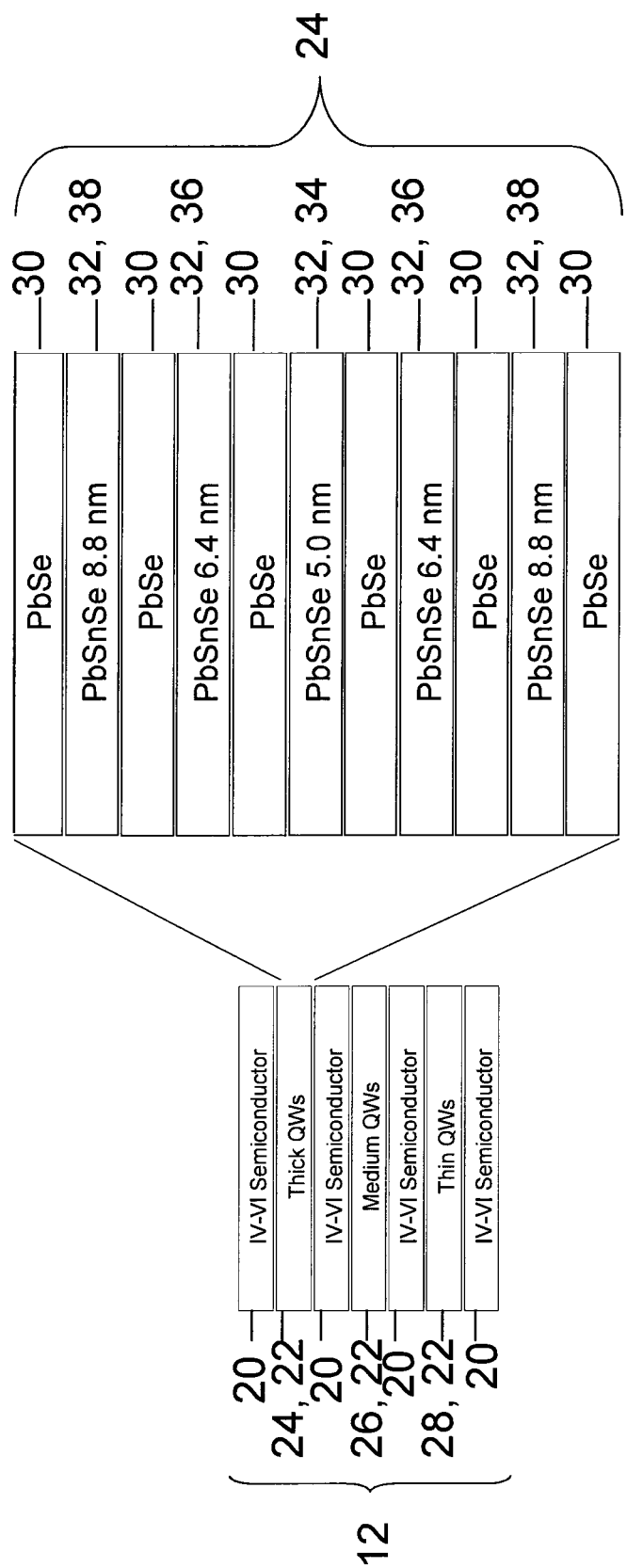
FIG. 13. A cross-sectional drawing of the embodied mid-IR detection device showing an example structure of a thick quantum well layer.

FIG. 13 shows one non-limiting example of an embodied thick QW layer 24 that would be near the colder side of the cooling portion 12. The embodied thick QW layer 24, shown has alternating PbSrSe 30 and PbSnSe 32 QWs 22. The sub-band energy created by the 5.0 nm thick PbSnSe QW 34 will be about 37 meV above the bottom of the conduction band in the IV-VI semiconductor layers 20 on either side of this thick QW layer 24. The slightly thicker PbSnSe QWs 36, 38 on either side of this thinnest QW 34, 6.4 nm and 8.8 nm, create sub-bands that are lower in energy, 30 meV and 24 meV, respectively, above the bottom of the conduction band in the IV-VI semiconductor layers 20 on either side of this thick QW layer 24. The 6 meV and 7 meV differences in these sub-band energies are similar to the acoustic phonon energies in IV-VI semiconductor materials. This design facilitates the transfer of thermal energy from the detection portion 8 of the crystalline lattice since the moving charge carriers can absorb these heat-containing phonons. The stair-step-like increase in sub-band energy levels thus enhances the thermoelectric cooling effect.

Figure 14:
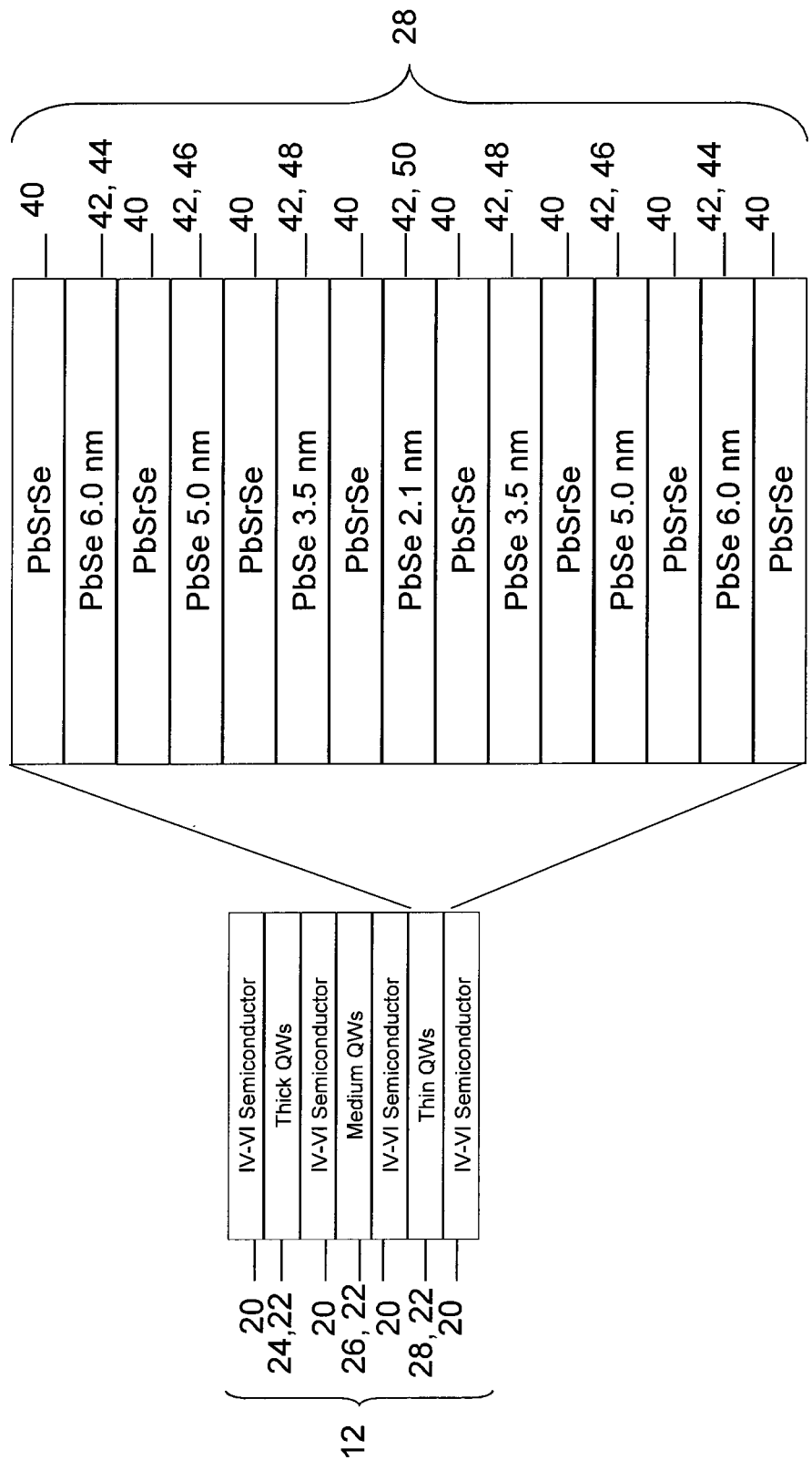
FIG. 14. A cross-sectional drawing of the embodied mid-IR detection device showing an example structure of a thin quantum well layer.

FIG. 14 shows one non-limiting example of a similar variation of QW width for a thin QW layer 28. In this case the PbSe QW material 42 becomes as thin as 2.1 nm 50, which creates a sub-band energy that is 75 meV above the bottom of the conduction band in the IV-VI semiconductor layers 20 on either side of this thin QW layer 28. The other PbSe QW 42 thicknesses of 3.5 nm 48, 5.0 nm 46, and 6.0 nm 44 create sub-band energies of 65 meV, 52 meV, and 46 meV, respectively. The energy differences between these sub-bands, which are as large as 13 meV, are effective in enhancing thermoelectric performance since these match the energies of optical phonons and their easy absorption assist inter-sub-band charge carrier transitions.

7. Fabrication Methods

Figure 15:
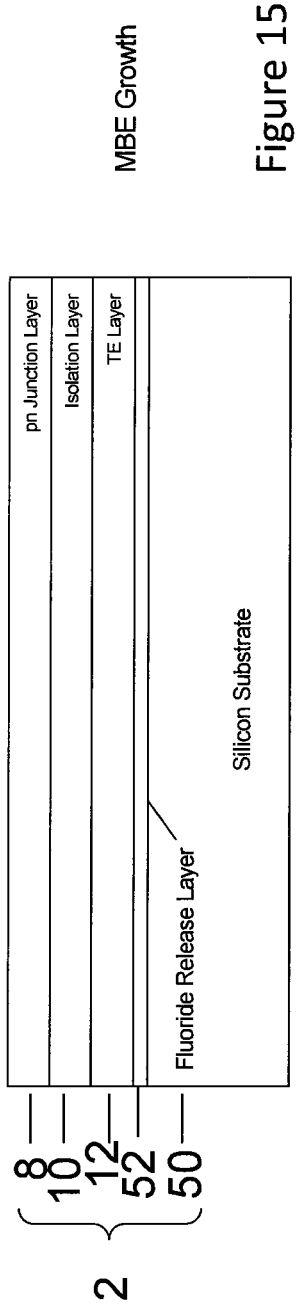
FIG. 15. Includes FIGS. 15a-15j which depict an embodied sequence of fabrication methods used to obtain an embodied mid-IR detection device.
Figure 15:
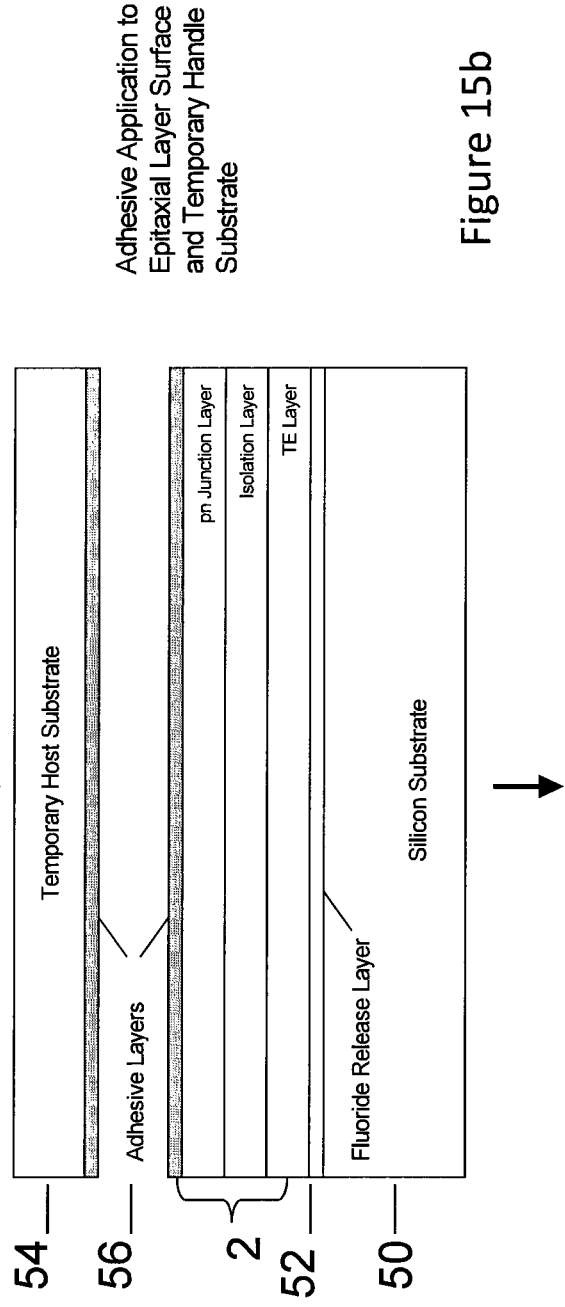

FIG. 15, consisting of FIGS. 15a-15j outlines one embodiment of a sequence of fabrication actions that can be used to obtain the mid-IR photovoltaic sensor 1 described above. Procedures for growth and processing of these layers, including the QWs 22 inside the cooling portion 12, are known in the art. However, the embodied fabrication of the embodied sensors and detection apparatus as described herein are novel. The mid-IR detection device 2 can include, in one embodiment, a combination of PbSrSe, PbSe, or PbSnSe. For example, a detector designed for acetaldehyde detection at 1727 $cm^{-1}$ can be made using a PbSnSe alloy with a tin content of 2% or greater. As shown in FIG. 15a the embodied mid-IR detection device 2 can be constructed of IV-VI semiconductor material grown on a (111)-oriented silicon substrate 50 using a fluoride buffer layer 52 consisting of a 2 nm thick $CaF_2$ layer grown directly on the silicon, following native oxide desorption, and approximately 30 nm of $BaF_2$. Use of industry standard silicon substrates and production MBE or MOCVD methods make this a manufacturing-friendly growth technology and thus suitable for obtaining low cost devices. It should also be understood that the substrate 50 can be constructed of other types of materials including $BaF_2$, for example.

Figure 15C:
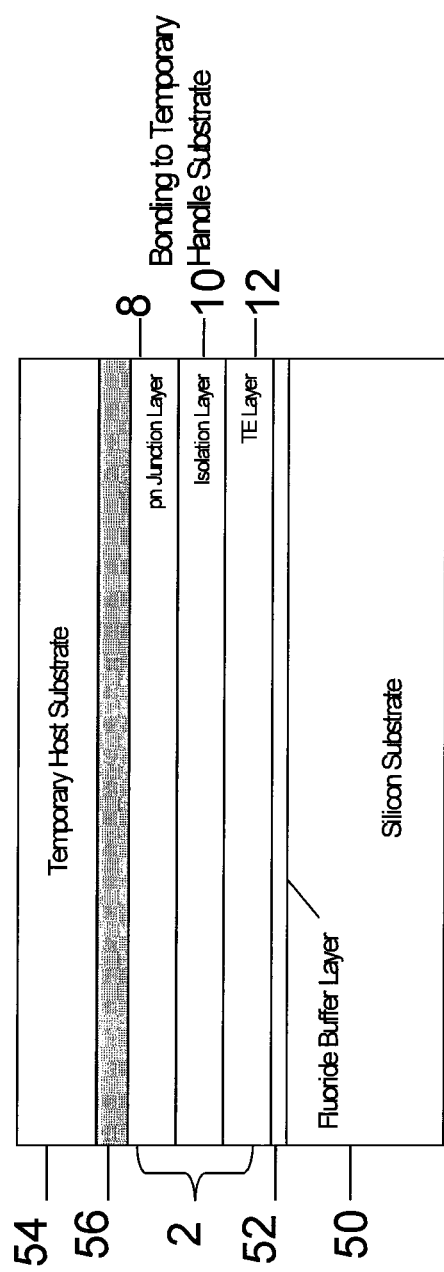
Figure 15D:
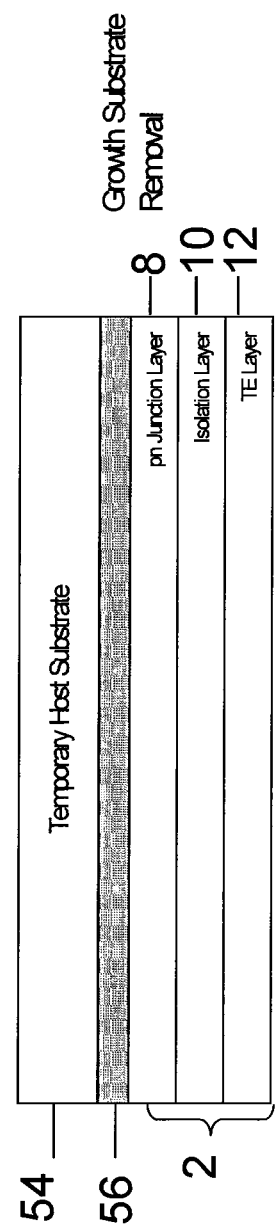

The next action shown in FIG. 15b includes the application of an adhesive material 56 to at least one of the top of the MBE-grown mid-IR detection device 2 and a temporary handle substrate 54. This adhesive material 56 may comprise of a polymer that can be easily dissolved with a solvent. For example, photoresist, which can be dissolved with acetone, can be used. FIG. 15c demonstrates the mid-IR detection device 2 and temporary handle substrate 54 bonded together, then FIG. 15d shows the structure after the silicon growth substrate 50 is removed by dissolving the $BaF_2$ 52 release layer in water. FIG. 15e shows the deposition of metal bonding layers 6 to the exposed bottom of the MBE-grown IV-VI mid-IR detection device 2 and the surface of the heat sink 4 which can be constructed of a metal such as copper or aluminum. The deposited metals can include indium, tin, and bismuth, for example. Next, FIG. 15f shows the IV-VI semiconductor mid-IR detection device 2 bonded to the heat sink 4 after removal of the temporary handle substrate 54. The bonding step can be performed under vacuum conditions and at temperatures below 150° C. with the appropriate In/Sn/Bi eutectic alloy compositions, for example.

The next steps in the mid-IR detection device 2 fabrication procedure may involve two separate mesa etching actions to allow independent electrical access to the underlying cooling portion 12, e.g., the TE layer (as shown in FIG. 15g) and the underlying n-type layer 8b (as shown in FIG. 15h) when the detection portion 8 is implemented as the pn junction photodetector. Standard photolithographic patterning is used to enable selective removal of the IV-VI semiconductor material. Wet or dry etching procedures can be used to perform the mesa etches. FIG. 15i shows the deposition of an electrically insulating passivation layer 60 over the entire mid-IR detection device 2. This passivation layer 60 can also function as an antireflective coating layer if its thickness is ¼ of the wavelength of the mid-IR light inside the passivation layer. Suitable passivation layer materials can include $SiO_2$, $Si_3N_4$, $CaF_2$, or parylene. The final action shown in FIG. 15j shows photolithographic patterning for the selective etching of contact vias through the electrically insulating passivation layer 60 and formation of metal contacts 14 to the p-type layer 8a and n-type layer 8b in the detection portion 8 and the top of the cooling portion 12, e.g., the TE layer.

8. Apparatus—a QCL-Based Instrument for Measuring Gas Phase Acetaldehyde

The focused feature in developing a TLAS system that can measure biomarkers in gas phase including, but not limited to, gas phase acetaldehyde is the mid-IR laser that is required to excite the vibrational modes of the molecule. The main problem with conventional IV-VI (lead-salt) mid-IR lasers (used in the previous prototypes) associated with the prior art is the requirement for cryogenic cooling to obtain continuous wave (cw) emission. Recent commercial availability of high performance mid-IR lasers based on state-of-the-art cryogenic-free quantum cascade laser (QCL) designs has made development of an improved TLAS instrument possible. The primary components of a QCL-based TLAS system are a QCL, high heat load heat sink mount with an integrated thermoelectric cooling module, a long optical path gas cell, a mid-IR detection device, control electronics with user interface (such as keyboard or keypad and a display), and a vacuum pump, such as a small oil-free mechanical vacuum pump. QCLs with continuous wave (cw) emission in the region of the carbonyl stretch mode of acetaldehyde (1750 $cm^{-1}$) are commercially available. For example, Alpes Lasers offers a QCL that operates in cw mode at a heat sink between −30° C. and −20° C. with a 10 volt bias and >500 mA injection current. This laser can be operated with a compact thermoelectric cooling module. By contrast, the TLAS instrument developed by Kamat et al. used a IV-VI semiconductor mid-IR diode laser that required cryogenic cooling to below 110 K, and this necessitated use of a bulky (and unreliable) closed-cycle compressor system. Based on what is now known about the Warburg effect it is clear that having a reliable way to measure trace concentrations of gas phase acetaldehyde will lead to a better understanding of metabolic energy flow mechanisms in biological systems, which in turn will facilitate cancer drug discovery, cancer therapy management, and detection of cancer at earlier stages than previously possible.

9. Overview of an Embodied TLAS Instrument

Tunable laser absorption spectrometry is a high spectral resolution technique capable of detecting specific molecular species at ultra-low concentrations. Gas samples can be measured in real-time without the need for sample preparation thus reducing complexity (and eliminating possible analyte loss due to reaction chemistry) compared to traditional trace gas sensing technologies such as GC/MS. A mid-IR tunable laser absorption spectrometer (TLAS) system includes three main components: 1) a laser source, 2) a gas cell defining a detection space, and 3) a detector. In general, the laser source produces a laser beam that is projected through a least a portion of the detection space and is used to interrogate the gas sample of interest in the gas cell. If the molecule of interest (e.g., a biomarker) is present, the beam will be absorbed at a very specific wavelength unique to that particular molecule. The detector generates a signal in which a wavelength of absorption of the beam is indicative of a specificity of the molecule, and wherein a magnitude of the signal is proportional to a concentration of the molecule in the gaseous sample.

Figure 16:
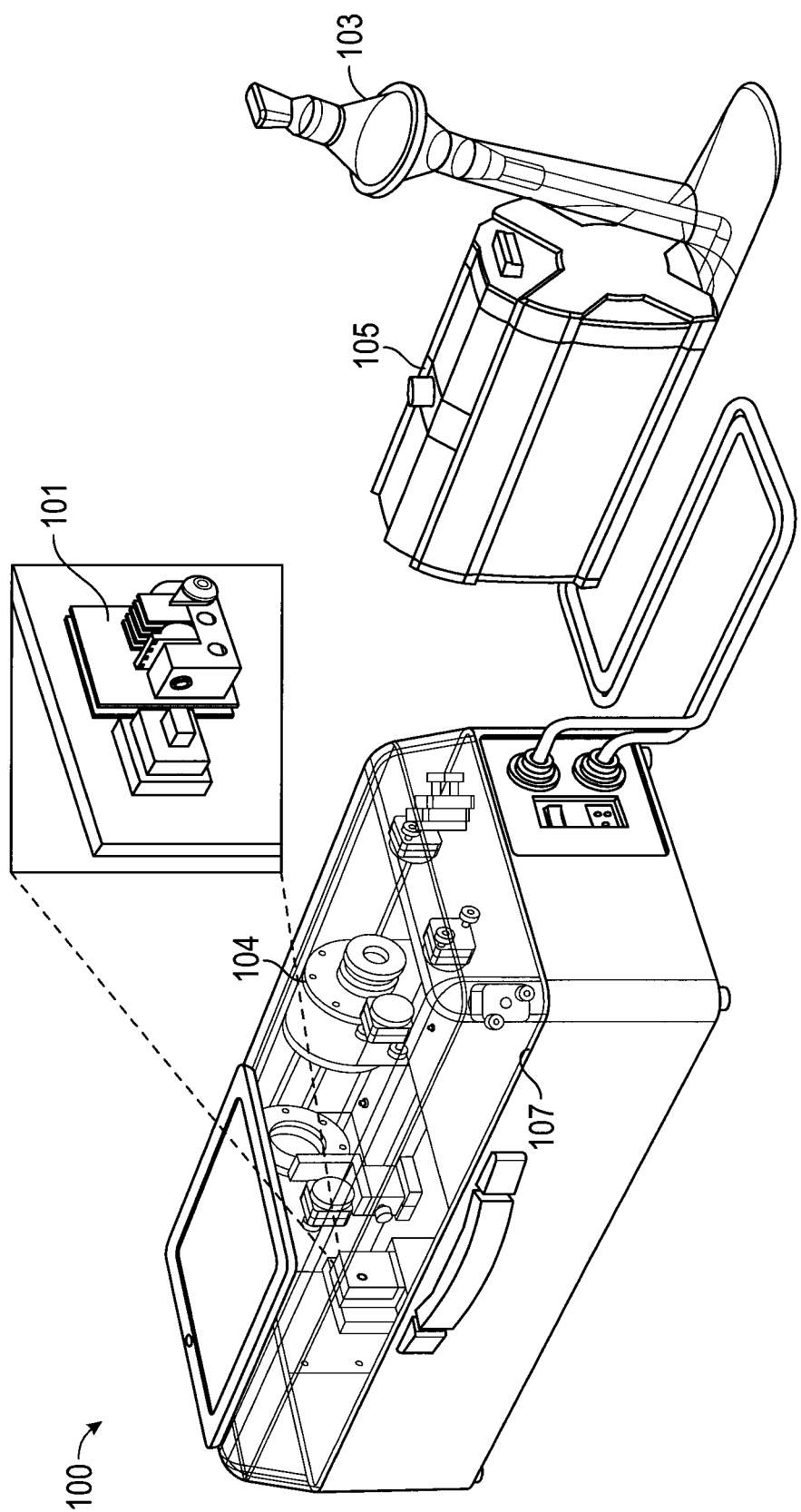
FIG. 16. Artist's perspective-view depiction of an embodied TLAS instrument for exhaled acetaldehyde measurement.

FIG. 16 shows a computer aided design (CAD) block drawing of one embodiment of a TLAS instrument 100 constructed in accordance with the present disclosure. The TLAS instrument 100 may be provided with, for example, a mid-IR photovoltaic sensor 101, a mouth piece 103 for collecting exhaled breath from a subject, a gas cell 104, a pump 105, a case 107 in which the mid-IR photovoltaic sensor 101, the gas cell 104, and a mid-IR laser 109 is disposed. The mid-IR photovoltaic sensor 101 can be constructed identically as the mid-IR photovoltaic sensor 1 described above. The mouth piece 103 is coupled to the gas cell 104 and the pump 105 via tubing, for example. The mouth piece 103 may be used to collect exhaled breath from a subject, which is then moved into a detection space 110 (see FIG. 17) by the pump 105 for analysis. The detection space 110 is at least partially surrounded or encompassed by the gas cell 104 by the pump 105 for analysis. The mid-IR laser 109 (See FIG. 17) is configured to project a beam of electromagnetic energy having an infrared spectrum through at least a portion of the detection space. The mid-IR photovoltaic sensor 101 includes the detection portion 8 of the mid-IR detection device 2 that is configured as a photovoltaic detector and positioned relative to the mid-IR laser 109 to receive at least a portion of the beam of electromagnetic energy, the detection portion 8 generating thermal energy responsive to receipt of the beam of electromagnetic energy.

Figure 17:
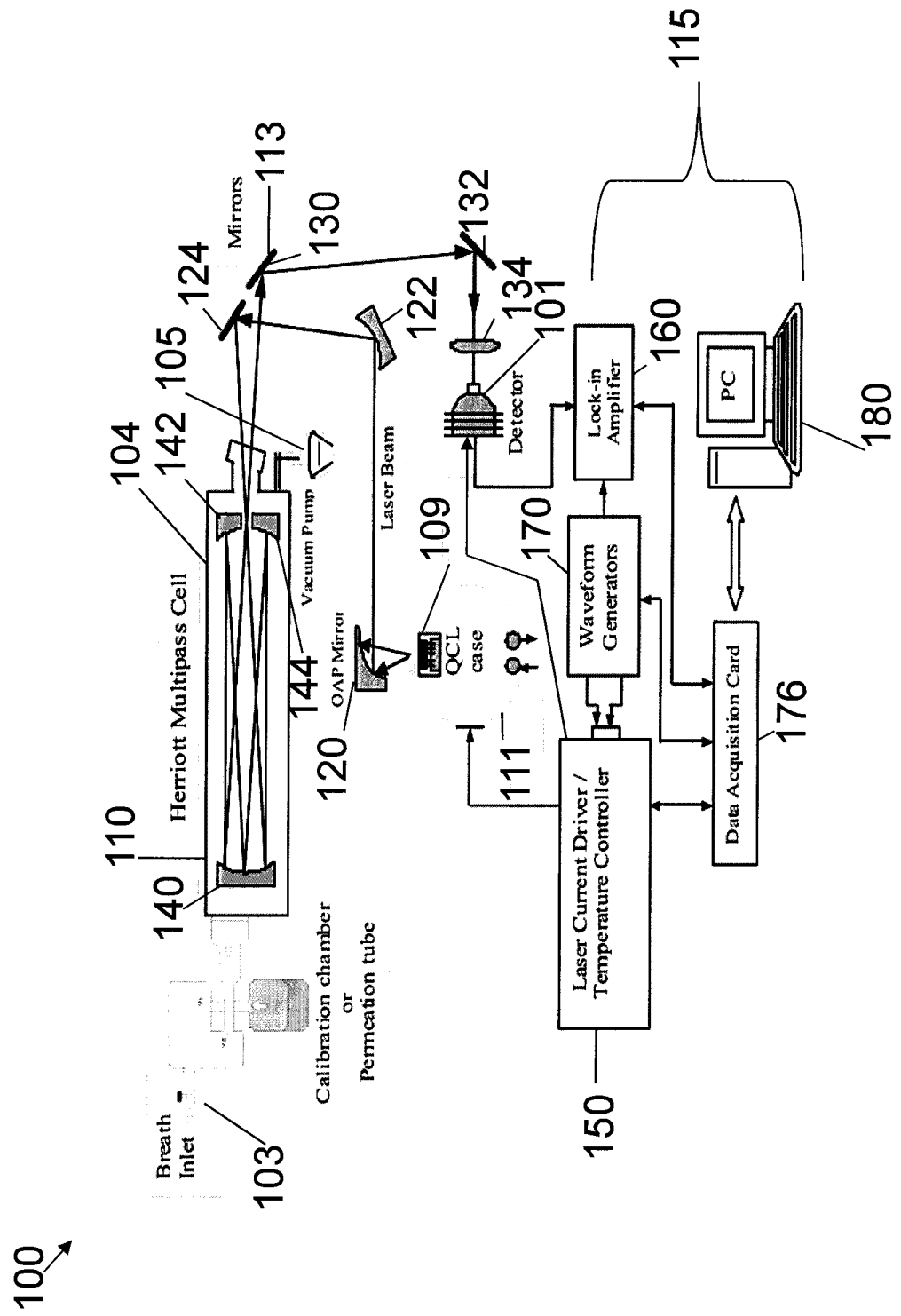
FIG. 17. Schematic drawing of an embodied TLAS system designed for measuring exhaled trace gases (biomarkers) in breath.

FIG. 17 is a schematic diagram of the TLAS instrument 100 wherein a QCL emitting a laser beam (for example having a wavelength around 6 μm, or any other mid-IR wavelength) is used as the mid-IR laser 109. The TLAS instrument 100 includes the mid-IR laser 109, a case 111 to package and protect the mid-IR laser 109, optics 113 and control electronics 115. The optics 113 direct the laser beam produced by the mid-IR laser 109 into the detection space 110 of the gas cell 104. As shown in FIG. 17, the optics 103 may include three mirrors 120, 122 and 124 for directing the laser beam from the mid-IR laser 109 into the detection space 110. However, more or less mirrors may be used depending upon the desired location of the Mid IR laser 109 relative to the gas cell 104 and the detection space 110. The optics 113 also direct the laser beam out of the detection space 110 and to the mid-IR photovoltaic sensor 101.

As shown in FIG. 17, the optics 103 may include two mirrors 130 and 132, as well as a lens 134 that work together for directing the laser beam from the detection space 110 to the mid-IR photovoltaic sensor (a.k.a., detector) 101. However, more or less mirrors may be used depending upon the desired location of the mid-IR photovoltaic sensor 101 relative to the gas cell 104 and the detection space 110. The lens 134 focuses the laser beam onto the detection portion 8 of the of the mid-IR detection device 2. The gas cell 104 may be a long optical pathlength multipass gas cell having one or more mirrors 140, 142 and 144 that direct the laser beam back and forth across the detection space 110 as shown in FIG. 17. In general, the sensitivity of the TLAS instrument 100 is proportional to the number of passes of the laser beam across the detection space 110 such that the laser beam may contact more of the gaseous sample. In one non limiting embodiment the gas cell 104 can be implemented as a herriott multipass cell having a path length in a range of, for example, about 10 meters to about 200 meters. The control electronics 115 may include a laser current and temperature controller 150, a lock-in amplifier 160, a waveform generator unit 170, a data acquisition card 176 and a computer 180.

The laser current and temperature controller 150 is coupled to the mid-IR laser 109 and the mid-IR photovoltaic sensor 101 via any suitable communication path. The laser current and temperature controller 150 may include one or more processors that generate control signals for actuating and controlling the wavelength of the mid-IR laser 109 so that one or more predetermined wavelength regions are interrogated for subjecting the gaseous sample to laser absorption spectrometry. The laser current and temperature controller 150 also transmits electrical control signals to the electrical contacts 14 of the cooling portion 12 of the mid-IR detection device 2 of the mid-IR photovoltaic sensor 101 depicted in FIG. 17 to cause the cooling portion 12 to actively move the thermal energy away from the detection portion 8 by moving the charge carriers as discussed herein previously. The waveform generator 170 is used to modulate the laser 109 at a specific frequency, which is typically between 10 kHz and 100 kHz. The lock-in amplifier 160 samples the detector signal at a frequency that is twice the laser modulation frequency. This method, which is called second harmonic detection, increases the molecular detection sensitivity of the sensor. The data acquisition card 176 converts the analog signal from the lock-in amplifier to a digital signal for subsequent processing by the computer.

The computer 180 has a non-transitory computer readable medium (not shown) and at least one processor. The non-transitory computer readable medium can be read only memory or random access memory and stores computer executable code that causes the at least one processor to receive (1) first data generated by the laser current and temperature controller 150 indicative of the wavelength of the laser beam, and (2) second data detected by the mid-IR photovoltaic sensor 101 indicative of absorption of predetermined wavelengths. The computer executable code, when executed by the at least one processor calculates a concentration of a biomarker within the gas-cell 104 based on the first data and the second data. In particular, the first data is used by the at least one processor to determine a wavelength of absorption of the laser beam and is indicative of a specificity of the biomarker. The second data is used by the at least one processor to determine a concentration of the biomarker in the gaseous sample. For example, in some embodiments, a magnitude of the second data is proportional to a concentration of the biomarker in the gaseous sample.

Although the preceding description has been described herein with reference to particular means, materials and embodiments, it is not intended to be limited to the particulars disclosed herein; rather, it extends to all functionally equivalent structures, methods and uses, such as are within the scope of the appended claims.

What is claimed is:
1. A detection apparatus comprising:
   a gas-cell defining a detection space;
   a mid-IR laser configured to project a beam of electromagnetic energy having an infrared spectrum through at least a portion of the detection space; and a mid-IR detection device formed of a monolithically integrated crystalline structure comprising:
   a detection portion configured as a photovoltaic detector and positioned relative to the mid-IR laser to receive at least a portion of the beam of electromagnetic energy and to generate an electrical signal responsive to receipt of the beam of electromagnetic energy;
   a cooling portion configured to receive a stimulus and actively move thermal energy away from the detection portion with aid of the stimulus; and
   an isolation portion between the detection portion and the cooling portion, the isolation portion electrically isolating the detection portion from the cooling portion, wherein the isolation portion comprises a group IV-VI semiconductor compound or alloy that is grown without intentional doping.

2. The detection apparatus of claim 1, wherein the detection portion comprises one or more layers forming a photovaic pn junction comprising an n-type section and a p-type section.

3. The detection apparatus of claim 2, further comprising independent electrical contacts attached to the n-type section, p-type section, and cooling portion.

4. The detection apparatus of claim 2, wherein the detection portion comprises at least one of a group IV-VI semiconductor compound or alloy having a narrow bandgap between about 100 meV and about 500 meV.

5. The detection apparatus of claim 4, wherein the group IV-VI semiconductor compound or alloy is selected from a group consisting of PbSe, PbTe, PbSnSe, and PbSnSeTe.

6. The detection apparatus of claim 1, wherein the cooling portion comprises a thermoelectric layer having a series of spatially disposed quantum well sub-layers.

7. The detection apparatus of claim 1, wherein the group IV-VI semiconductor compound or alloy of the isolation portion comprises at least one of PbSrSe and PbSrSeTe.

8. The detection apparatus of claim 1, wherein the detection portion, cooling portion, and isolation portion are grown of group IV-VI semiconductor layers during a single molecular beam procedure, wherein the group IV-VI semiconductor layers are lattice matched or substantially lattice matched.

9. The detection apparatus of claim 8, wherein the group IV-VI semiconductor layers are substantially lattice matched and comprise a mismatch of greater than 0% and less than or equal to about 2%.

10. The detection apparatus of claim 1, wherein the cooling portion comprises a semiconductor material having appropriate doping levels to achieve electron or hole concentrations in a range of $1 \times 10^{18}$ cm$^{-3}$ to $1 \times 10^{19}$ cm$^{-3}$, and wherein the stimulus induces charge carrier flow within the cooling portion so as to transport the thermal energy in a direction of charge carrier flow.

11. The detection apparatus of claim 1, wherein the cooling portion comprises a semiconductor material having appropriate doping levels to achieve electron or hole concentrations in a range of $2 \times 10^{18}$ cm$^{-3}$ to $4 \times 10^{18}$ cm$^{-3}$, and wherein the stimulus induces charge carrier flow within the cooling portion so as to transport the thermal energy in a direction of charge carrier flow.

12. The detection apparatus of claim 1, wherein the cooling portion comprises a group IV-VI semiconductor matrix material selected from a group consisting of a IV-VI semiconductor compound, IV-VI alloy, and IV-VI superlattice.

13. The detection apparatus of claim 12, wherein the matrix material includes a series of spatially disposed quantum well sub-layers.

14. The detection apparatus of claim 13, wherein the series of quantum well sub-layers comprise a first quantum well sub-layer having a first thickness, and a second quantum well sub-layer having a second thickness, and wherein the first quantum well sub-layer is between the detection portion and the second quantum well sub-layer, the first thickness being greater than the second thickness.

15. The detection apparatus of claim 14, wherein the first thickness is in a range from 7 nm to 10 nm, and wherein the second thickness is in a range from 1 nm to less than 7 nm, such that the first quantum well sub-layer provides a first energy barrier to charge carrier flow, and the second quantum well sub-layer provides a second energy barrier to charge carrier flow, the second energy barrier greater than the first energy barrier.

16. The detection apparatus of claim 15, wherein at least one of the first and second energy barriers is in a range of about 50 meV to about 75 meV tall when at least one of the first quantum well sub-layer and the second quantum well sub-layer is at a temperature between about 65° F. and about 85° F., the second thickness is in a range from about 2 nm to about 6 nm, and the second quantum well sub-layer is constructed of a PbSe layer between PbSrSe layers.

17. The detection apparatus of claim 13, wherein the quantum well sub-layers include PbSe wells surrounded by PbSrSe.

18. The detection apparatus of claim 13, wherein the quantum well sub-layers comprised of PbSnSe wells having a first bandgap surrounded by PbSe having a second bandgap larger than the first bandgap.

19. The detection apparatus of claim 18, wherein the quantum well sub-layers have thicknesses in a range from about 1 nm to about 10 nm.

20. A method of analyzing a gaseous sample, comprising:
   providing a tunable laser adsorption spectrometer system comprising a detection apparatus for generating an electrical signal, the detection apparatus comprising,
      a gas-cell defining a detection space;
      a mid-IR laser configured to project a beam of electromagnetic energy having an infrared spectrum through at least a portion of the detection space; and
      a mid-IR detection device formed of a monolithically integrated crystalline structure comprising:
         a detection portion configured as a photovoltaic detector and positioned relative to the mid-IR laser to receive at least a portion of the beam of electromagnetic energy and to generate an electrical signal responsive to receipt of the beam of electromagnetic energy;
         a cooling portion configured to receive a stimulus and actively move thermal energy away from the detection portion with aid of the stimulus; and
         an isolation portion between the detection portion and the cooling portion, the isolation portion electrically isolating the detection portion from the cooling portion, wherein the isolation portion comprises a group IV-VI semiconductor compound or alloy that is grown without intentional doping; and
   providing the gaseous sample to the detection apparatus and detecting a presence or absence and/or measuring a concentration of an analyte in the gaseous sample.

21. The method of claim 20, wherein a wavelength of absorption of a laser beam is indicative of a specificity of the analyte, and wherein a magnitude of the electrical signal is proportional to the concentration of the analyte in the gaseous sample.

22. The method of claim 20, wherein the gaseous sample is exhaled breath.

23. The method of claim 20, wherein the gaseous sample is collected from an atmosphere in proximity to a skin of a patient.

24. The method of claim 20, further comprising the step of comparing the electrical signal obtained with a control signal.

25. The method of claim 20, wherein the analyte is a biomarker.

26. The method of claim 20, wherein the analyte is acetaldehyde.

27. A gas sensor apparatus comprising:
a detection apparatus comprising:
a gas-cell defining a detection space;
a mid-IR laser configured to project a beam of electromagnetic energy having an infrared spectrum through at least a portion of the detection space; and
a mid-IR detection device formed of a monolithically integrated crystalline structure comprising:
a detection portion configured as a photovoltaic detector and positioned relative to the mid-IR laser to receive at least a portion of the beam of electromagnetic energy and to generate an electrical signal responsive to receipt of the beam of electromagnetic energy;
a cooling portion configured to receive a stimulus and actively move thermal energy away from the detection portion with aid of the stimulus; and
an isolation portion between the detection portion and the cooling portion, the isolation portion electrically isolating the detection portion from the cooling portion, wherein the isolation portion comprises a group IV-VI semiconductor compound or alloy that is grown without intentional doping; and
electronics coupled to the detection portion and cooling portion, the electronics configured to receive data signals from the detection portion, and to provide the stimulus to the cooling portion.

28. The gas sensor apparatus of claim 27, wherein the electronics includes a computer having a non-transitory computer readable medium storing computer executable code that causes at least one processor to calculate a concentration of a biomarker within the gas-cell.

29. The gas sensor apparatus of claim 27, further comprising a pump for moving a gaseous sample into the detection space.

30. The gas sensor apparatus of claim 29, wherein the gaseous sample is collected from an atmosphere in proximity to a skin of a patient, or is exhaled breath.

31. The gas sensor apparatus of claim 27, wherein the group IV-VI semiconductor compound or alloy of the isolation portion of the detection apparatus comprises at least one of PbSrSe and PbSrSeTe.

32. A mid-IR detection device comprising:
a detection portion configured as a photovoltaic detector to receive at least a portion of a beam of electromagnetic energy and to generate an electrical signal responsive to receipt of the beam of electromagnetic energy;
a cooling portion configured to receive a stimulus and actively move thermal energy away from the detection portion with aid of the stimulus;
an isolation portion between the detection portion and the cooling portion, the isolation portion electrically isolating the detection portion from the cooling portion, wherein the isolation portion comprises a group IV-VI semiconductor compound or alloy that is grown without intentional doping, and wherein the detection portion, the cooling portion and the isolation portion are formed as a monolithically integrated crystalline structure;
a first set of electrical contacts on the detection portion and configured to receive the electrical energy; and
a second set of electrical contacts on the cooling portion and configured to provide the stimulus.

33. The mid-IR detection device of claim 32, wherein the group IV-VI semiconductor compound or alloy of the isolation portion comprises at least one of PbSrSe and PbSrSeTe.

* * * * *